(12) United States Patent
Chen et al.

(10) Patent No.: US 7,538,329 B2
(45) Date of Patent: May 26, 2009

(54) ENERGY-TRANSFER NANOCOMPOSITE MATERIALS AND METHODS OF MAKING AND USING SAME

(75) Inventors: Wei Chen, Stillwater, OK (US);
Shaopeng Wang, Stillwater, OK (US);
Sarah Westcott, Stillwater, OK (US);
Jun Zhang, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 265 days.

(21) Appl. No.: 11/262,470

(22) Filed: Oct. 28, 2005

(65) Prior Publication Data

US 2007/0063154 A1 Mar. 22, 2007

Related U.S. Application Data

(60) Provisional application No. 60/649,406, filed on Feb. 2, 2005.

(51) Int. Cl.
*G01T 1/20* (2006.01)
(52) U.S. Cl. .............. 250/370.11; 977/904; 977/905; 250/370.07; 250/459.1; 436/58; 436/904
(58) Field of Classification Search .............. None
See application file for complete search history.

(56) References Cited

U.S. PATENT DOCUMENTS

| | | | |
|---|---|---|---|
| 5,006,714 A * | 4/1991 | Attix | 250/368 |
| 5,606,163 A | 2/1997 | Huston et al. | |
| 5,656,815 A | 8/1997 | Justus et al. | |
| 5,952,665 A | 9/1999 | Bhargava | |
| 6,300,640 B1 | 10/2001 | Bhargava et al. | |
| 6,514,772 B2 * | 2/2003 | Siiman et al. | 436/518 |
| 7,009,181 B1 * | 3/2006 | Miller et al. | 250/358.1 |
| 7,067,072 B2 * | 6/2006 | Chen | 252/301.6 S |
| 2003/0030067 A1 * | 2/2003 | Chen | 257/102 |
| 2003/0064532 A1 | 4/2003 | Chen | |
| 2004/0238757 A1 * | 12/2004 | Gaza et al. | 250/484.5 |
| 2006/0118757 A1 * | 6/2006 | Klimov et al. | 252/62.51 R |
| 2006/0239907 A1 * | 10/2006 | Luzzi et al. | 424/1.11 |
| 2007/0111324 A1 * | 5/2007 | Nie et al. | 436/518 |

OTHER PUBLICATIONS

Bhargava, R.N., "Doped nanocrystalline materials—Physics and applications", Journal of Luminescence, Elsevier, vol. 70, 1996, pp. 85-94.*

(Continued)

*Primary Examiner*—David P Porta
*Assistant Examiner*—Yara B Green
(74) *Attorney, Agent, or Firm*—Dunlap Codding, P.C.

(57) ABSTRACT

The presently claimed and disclosed inventions relate, in general, to methods of radiation dosimetry and imaging using scintillation luminescence. More particularly, materials having a scintillation luminescence response to radiation that varies with total radiation dose received can be used for dosimetry monitoring, including, but not limited to nanoparticles for in vivo, real-time dosimetry. Energy-transfer nanocomposite materials as well as methods of making and using such materials in various applications including, but not limited to, in vivo radiation dosimetry and imaging, are disclosed. More particularly, the presently claimed and disclosed inventions relate to nanoparticle scintillation luminescence particles encapsulated in hosts of the general formula BaFX and BaFX:$Eu^{2+}$ where X=Cl, Br and I.

26 Claims, 18 Drawing Sheets

OTHER PUBLICATIONS

Chen, R. et al., "Dose dependence and dose-rate dependence of the optically stimulated luminescence signal", Journal of Applied Physics; vol. 89, No. 1; Jan. 1, 2001; pp. 259-263.*

Minet, O. et al., "Heat Stress Induced Redistribution of Fluorescent Quantum Dots in Breast Tumor Cells", Journal of Fluorescence; vol. 14, No. 3; May 2004; pp. 241-247.*

Torrisi, L., "Plastic scintillator investigations for relative dosimetry in proton-theraphy", Nuclear Instruments and Methods in Physics Research B 170, Elsevier, 2000; pp. 523-530.*

Thoms, M., "Method for the determination of photostimulable defect center concentrations, production rates, and effective formation energies", J. Appl. Phys. (1994) 75 (9): 4658-4661.

Gurvich et al., "Phosphors for Luminescent Image Plates", J. of X-Ray Science (1996) 48-62, Article No. 0003.

Peng et al., "Epitaxial Growth of Highly Luminescent CdSe/CdS Core/Shell Nanocrystals with Photostability and Electronic Accessibility", J. Am. Chem. Soc. (1997) 119, 7019-7029.

Ye et al., "Combustion Synthesis and Photoluminescence of Nanocrystalline $Y^2O^3$:Eu Phosphors", Elsevier Science Ltd. (1997) vol. 32, No. 5, 501-506.

Correa-Duarte et. al., "Stabilization of CdS semiconductor nanoparticles against photodegradation by a silica coating procedure", Elsevier Science Ltd. (1998) Chemical Physics Letters 286, 497-501.

Sudimack et al., "Targeted drug delivery via the folate receptor", Elsevier Science Ltd. (2000) Advanced Drug Delivery Reviews 41, 147-162.

Chen et al., "Luminescence enhancement of EuS nanoclusters in zeolite", American Institute of Physics (2000) Applied Physics Letters, vol. 76, No. 17, 2328-2330.

Gaponik et al., "Thiol-Capping of CdTe Nanocrystals: An Alternative to Organometallic Synthetic Routes", J. Phys. Chem. B (2002) 106, 7177-7185.

Chan et al., "Luminescent quantum dots for multiplexed biological detection and imaging", Elsevier Science Ltd. (2002) Current Opinion in Biotechnology, 13:40-46.

Zhang et al., "Surface modification of superparamagnetic magnetite nanoparticles and their intracellular uptake", Elsevier Science Ltd. (2002) Biomaterials 23, 1553-1561.

Wang et al., "Antigen/Antibody Immunocomplex from CdTe Nanoparticle Bioconjugates", Americal Chemical Society (2002) Nano Letters, vol. 2, No. 8, 817-822.

Leamon et al., "Folate-targeted chemotherapy", Elsevier Science Ltd. (2004) Advanced Drug Delivery Reviews 56, 1127-1141.

Chen et al., "Structure and luminescence of $BaFBr:Eu^{2+}$ and $BaFBr:Eu^{2+}$, $Tb^{3+}$ phosphors and thin films", American Institute of Physics 97 (2005) 083506-1-083506-8.

Joly et al., "Upconversion luminescence of CdTe nanoparticles", The American Physical Society (2005), Physical Review B 71, 165304-1-165304-9.

* cited by examiner

ENERGY-TRANSFER NANOCOMPOSITE MATERIALS AND METHODS OF MAKING AND USING SAME

RELATED APPLICATIONS

This applications claims priority under 37 CFR 35 U.S.C. 119(e) to U.S. provisional application, Ser. No. 60/649,406 filed Feb. 2, 2005 entitled "SCINTILLATION LUMINESCENCE DOSIMETRY APPARATUS AND METHODS OF MAKING AND USING SAME", the entire contents of which are hereby incorporated by reference in their entirety as if set forth explicitly herein.

GOVERNMENTAL RIGHTS

The government may have certain rights in and to the presently disclosed inventions pursuant to NSF Contract Number DMI-0132030, and NIH Contract Numbers 1 R43 AI52937-01, 1 R43 CA110091-01, and 1 R43 CA112756-01.

BACKGROUND OF THE INVENTION

All references to patent applications, issued patents, articles, trade journals and manuals are expressly intended to incorporate such materials expressly herein in their entirety as if set forth specifically herein. The above listed materials are only provided as examples and should not be regarded as limiting to the type of materials expressly incorporated herein.

1. Field of the Invention

The presently claimed and disclosed inventions relate, in general, to methods of radiation dosimetry and imaging using scintillation luminescence. More particularly, materials having a scintillation luminescence response to radiation that varies with total radiation dose received can be used for dosimetry monitoring, including, but not limited to nanoparticles for in vivo, real-time dosimetry. Energy-transfer nanocomposite materials as well as methods of making and using such materials in various applications including, but not limited to, in vivo radiation dosimetry and imaging, are disclosed. More particularly, the presently claimed and disclosed inventions relate to nanoparticle scintillation luminescence particles encapsulated in hosts of the general formula BaFX and BaFX:$Eu^{2+}$ where X=Cl, Br and I.

2. Background

In the presently disclosed invention, special characteristics of materials are used to generate scintillation luminescence (SL), meaning the emission of light (UV, visible, near IR, or IR wavelengths) in response to radiation. SL is also known in the art as X-ray luminescence, although other forms of radiation such as gamma ray, alphas, betas, neutrons, pi-mesons, ions (carbon and neon) and positrons can also cause SL.

When X-rays are used for imaging (for example, medical or security or non-destructive evaluation), the detection of the X-rays is done by several methods. For example, the use of a film is very common, sometimes in conjunction with a scintillator to convert the X-rays to visible light. Scintillators are also used with CCD cameras (charge-coupled device) for the digital acquisition of images. In general, a scintillator must emit in a suitable wavelength range, have high efficiency, have high sensitivity, have a fast response and exhibit high transparency to the emitted light. Although there are many scintillator materials available, no one single scintillator provides the desired combination of stopping power (absorption coefficient), light output and decay time for every application.

The strong luminescence and ultra-fast decay lifetime of semiconductor nanoparticles have suggested that these types of materials may provide a new solution for the design and fabrication of high efficiency scintillators having rapid response rates. However, the stopping power of most semiconductors is low and their scintillation luminescence is very weak. By encapsulating semiconductor nanoparticles with materials with high stopping power and that transfer energy efficiently to the semiconductor nanoparticles (such as BaFX where X=Cl, Br, I), as in the presently disclosed and claimed invention, a new type of scintillator has been developed that has efficient emission, a fast response, and a selectable wavelength of emission. Additionally, with regard to the extensive use of X-ray and similar radiation technologies in the medical industry, manufacturing, security, inspection, non-destructive testing, and other applications, the use of nanocomposite materials holds the potential for higher resolution imaging at lower energy levels, resulting in substantial reductions in cost, complexity, hazards, and other negative aspects of the use of these processes.

Thus, it is presently disclosed and claimed that SL can be used in biomedical applications such as in vivo dosimetry and radiation dose imaging. In one aspect of the presently disclosed and claimed inventions, nanoparticles or bulk materials that emit SL upon exposure to radiation such as X-rays are injected into tumors with two possible outcomes. First, if the SL is stable and proportional to the radiation dose rate, then by measuring and integrating the amount of emission from these nanoparticles, the total X-ray dosage sustained by the tumor can be assessed, thus allowing the nanoparticles to serve as a real-time dosimeter. Second and more particularly, for materials in which the wavelength or intensity of one or more peaks in the SL change with radiation dose, those changes can be monitored to determine the dose.

In vivo radiation detection has additional requirements as well as strong scintillation luminescence. In vivo injection requires high solubility, stability in solution, little to no toxicity, biocompatibility, and no leakage within a biological environment. Additionally, the emission wavelengths are preferably detectable through tissues, requiring emission in a range from 700-1200 nm. These requirements are met by the use of nanoparticle SL for in vivo dosimetry, X-ray (and other energy source) imaging, radiation therapy dose control, and other applications.

DETAILED DESCRIPTION OF THE DISCLOSED INVENTIONS

Figure 1:
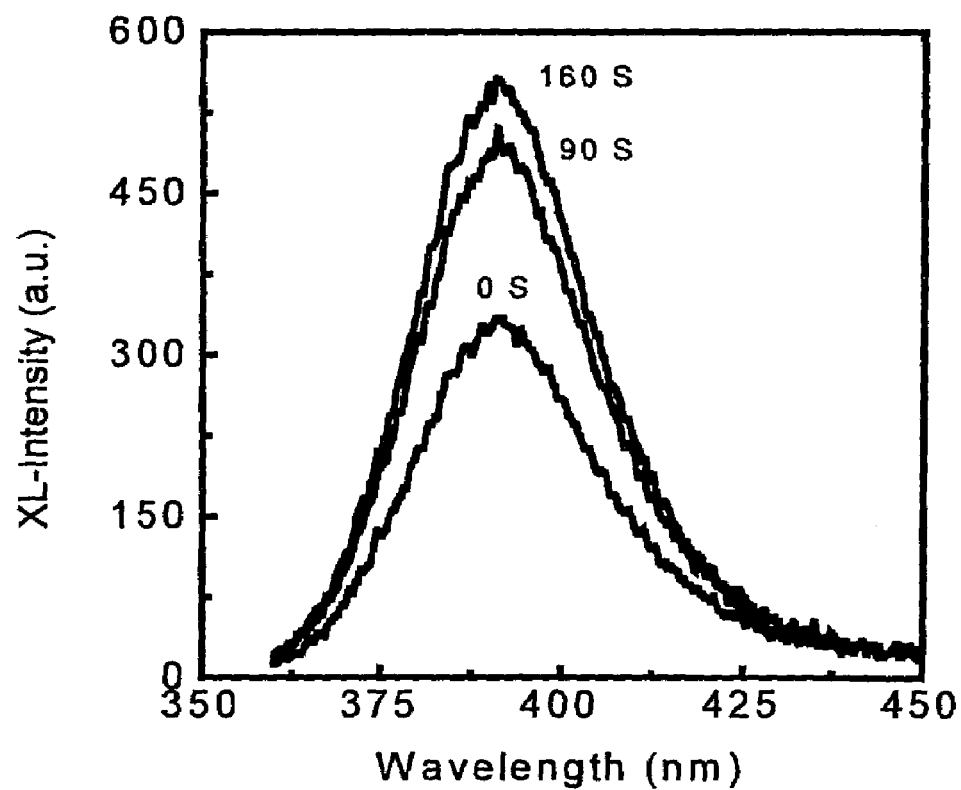
FIG. 1 shows the X-ray induced luminescence of BaFBr:$Eu^{2+}$, I phosphors (2% and 1% doping, respectively) initially (0 s, lowest) and after X-ray irradiation for 90 seconds (middle) and 160 s (top).

Before explaining at least one embodiment of the invention in detail, it is to be understood that the invention is not limited in its application to the details of construction and the arrangements of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

For radiation measurement, a scintillator must emit in a suitable wavelength range, exhibit high transparency to the emitted light, and have high efficiency, high sensitivity, and a rapid response time. The strong luminescence and ultra-fast decay lifetime of semiconductor nanoparticles provides for a novel approach to the design and fabrication of high efficiency scintillators having such a rapid response. Semiconductor nanoparticles, due to their small sizes, however, have poor stopping power and exhibit no or very weak scintillation luminescence. In the presently disclosed and claimed inventions, the enhancement of nanoparticle scintillation luminescence by encapsulation in hosts such as the family of BaFX and $BaFX:Eu^{2+}$ phosphors is shown. Energy transfer from such high stopping power hosts to the semiconductor nanoparticles leads to intense X-ray luminescence from, for example, CdTe nanoparticles in $BaFBr:Eu^{2+}$ phosphor hosts. Thus, these nanocomposite materials are a new type of efficient scintillator. For these and other materials, the X-ray excited luminescence intensity is dependent linearly on the radiation dose for a wide range of dosages, providing a novel dosimeter useful for real-time in vitro and in vivo dose detection and imaging. The market of medical therapy, such as radiotherapy and radiation diagnostics, is greatly impacted by such novel dosimeters.

Of the many diseases that threaten our lives, cancer ranks very high in terms of public fear. Much effort has been and continues to be dedicated to the treatment and eradication of the various types of cancer. The prognosis for someone diagnosed with cancer is actually not as dire as is commonly believed. Many cancers, such as early stage cancer of the larynx, childhood leukemia and Hodgkin's disease, are highly curable. Early in their development, malignant tumors are generally well localized. Any local treatments, such as surgical excision or radiation therapy, are indicated and highly successful. If the tumor is inaccessible or is intimately entwined with a vital anatomic structure or if regional spread of the cancerous cells has occurred, surgery may not be a feasible treatment option. In these cases, radiation therapy and chemotherapy may have better outcomes.

Currently, radiation therapy is still the most common and efficient treatment for cancers of all types. In North America, more than half of all cancer patients receive radiation therapy during the course of their illness. X-rays, protons, heavy particles such as neutrons, light ions such as carbon and neon, and pi-mesons have been used for radiation therapy. At present, the most common radiation source for radiotherapy treatment is high-energy X-rays. Radiation sources used to treat patients can be created from an external generator such as an X-ray tube or from radiopharmaceuticals that are injected into patients. The former is called teletherapy, in which the source of radiation is about 1 m away from the patient. The latter is known as brachytherapy, in which the radiation sources are implanted either in the tumor or very close to it. Brachytherapy has attracted a resurgence of interest in the medical world, primarily because it offers a simple procedure for delivering high radiation doses to a tumor but minimal doses to the surrounding healthy tissue.

Radiation works because it causes lethal damage to cells. In addition to primary damage from radiation, secondary electrons from radiation create highly reactive radicals in the intracellular compartment; with the result that these radicals chemically break bonds in cellular DNA and cause the cells to lose their ability to reproduce. Safety concerns are extremely important however, because radiation also kills healthy tissues as well as cancerous cells. Thus, although radiation is a valuable agent in the treatment of cancer, radiation can damage or destroy normal tissue and has the potential to induce mutations that can, in and of themselves, result in cancerous growth. Consequently, an important aspect of planning treatment is to arrange dose distribution so that critical organs near the target are at least partially avoided. The overall goal of treatment is to deliver a sufficiently fatal dose of radiation to the target while minimizing the damage to surrounding normal tissue. This is a challenge that continues to present difficulties. Basically, visualizing three-dimensional dose distribution in tissue is extremely difficult and in vivo measurement of radiation dose is not easy. Secondly, a fundamental problem in radiotherapy is the precise location and extent of the tumor mass.

As discussed herein, nanotechnology provides one or more alternative solutions to these issues presented by the treatment of cancerous tumors. Scintillation nanoparticles for visualizing dose distribution in vivo during radiation treatment may greatly improve the effectiveness of radiotherapy and, in doing so, improve the survival odds of cancer patients.

Radiation Detection

Traditional dosimeters such as plastic scintillation detectors, X-ray storage phosphor imaging plates, thermoluminescence dosimetry (TLD), and diodes work reasonably well, but could generally benefit from improvements in efficiency, response, and accuracy. For the most part, they are further limited to in vitro radiation dose measurement. TLD devices and silicon diodes can be used for in vivo patient dosimetry, but these applications are time consuming and awkward to implement. For example, a TLD device is typically implanted in a patient prior to treatment and then removed after radiotherapy, making it very inconvenient for routine patient management and care. After irradiation, the TLD device is removed, and the dosage absorbed is read using a heating system. Thus, such an approach does not support real-time dosimetry and its use is, therefore, generally limited to special patient care, such as total body irradiation. For treatment of a localized or deep-tissue tumor, the use of TLD systems is impossible or difficult.

Diode systems, on the other hand, can be read instantaneously—i.e., the radiation dose delivered to the area of treatment will be known immediately. Currently, available diode systems do, however, have several shortcomings, including positional and energy dependence. Studies have shown that for patients treated with electron beams, silicon diodes resulted in about 25% dose perturbation to the tissues beneath the diode. Additionally, the size of the diode system limits their in vivo applications. Currently, the smallest diode dosimetry system is 0.5 cm thick and 1 cm in diameter. Diode dosimeters are, therefore, suitable only for shallow implants or insertion into larger ducts, veins, passages and canals.

Nanoparticles scintillation has also been proposed for use in X-ray detection and imaging screens (e.g., U.S. Pat. Nos. 6,300,640; 5,952,665 which are incorporated explicitly herein by reference in their entirety). Each of these patents describes the use of such nanoparticle scintillation only in applications outside the body. Also, these patents disclose that while the scintillation luminescence intensity may be proportional to the instantaneous radiation dose, stability is more desirable in order that the wavelength and intensity response do not change with integrated radiation dose.

Thermoluminescence from nanocrystals embedded in a glass matrix has been used for determining radiation dose (e.g., U.S. Pat. No. 5,656,815; and U.S. Pat. No. 5,606,163 which are incorporated explicitly herein by reference in their entirety), but their use in these patents would not be considered a "real-time" measurement. While a fiber optic probe may be usable in vivo, it would require an incision and insertion into the body rather than through the injection of nanoparticles into the body as disclosed and claimed herein. Nanoparticles with photostimulated luminescence (PSL) properties have also been developed (e.g., U.S. application Ser. No. 10/223,764 which is incorporated explicitly herein by reference in its entirety) for radiation imaging. PSL is once again, not a "real-time" measurement and is likely to be used outside the body rather than in vivo.

The limitations of currently available in vivo dosimeters, such as requiring an excessive amount of time for a measurement and being too large for many desired applications, can be overcome through the use of nanoparticles, which are small enough to be placed virtually anywhere in the body and which provide a measurable luminescence response to X-rays. Furthermore, such a response is due to the widely understood property of scintillation luminescence.

Quantum Size Confinement and Advantages of Nanoparticles

As the size of a particle is reduced to approach the exciton Bohr diameter, there are drastic changes in the electronic structure and physical properties of the particle, such as a shift to higher band gap energy, the development of discrete features in the spectra, and a concentration of the oscillator strength into just a few transitions. These changes are referred to as quantum size confinement. Quantum size confinement not only increases the energy gap but also changes the densities of states.

Many novel physical properties and potential applications of semiconductor nanoparticles are related to the change in densities of states. Because the functionality of the nanoparticles in the presently disclosed and claimed inventions is X-ray dosimetry, it is convenient to consider the behavior of the nanoparticles relative to the functioning of phosphors such as those used in X-ray imaging plates. Luminescent nanoparticles may have higher quantum efficiency than conventional phosphors due to the large increase in electron-hole overlap, thus yielding an increase in the oscillator strength and, as a consequence, an enhancement of luminescence quantum efficiency. Furthermore, the emission decay lifetime of the nanoparticles is inversely proportional to the oscillator strength of a transition. Thus, the lifetime is shortened (often to the range of nanoseconds) with decreasing size due to the increase of the oscillator strength.

Strong evidence supporting the above referenced advantages of nanoparticles comes from the observation of ZnS: $Mn^{2+}$ and EuS nanoparticles. For example, bulk EuS at room temperature is not luminescent. Strong luminescence is observed, however, when EuS nanoparticles are formed in zeolite (W. Chen, X. Zhang, Y. Huang, Luminescence Enhancement of EuS Clusters in USY-Zeolite, Appl. Phys. Lett. 2000, 76 (17): 2328-2330 which is incorporated explicitly herein in its entirety by reference). High efficiency with short decay times makes nanoparticles a new type of fluorophore that has significant potential for biomedical applications. Recent research into the physical and chemical properties of nanoparticles suggests that the photophysical behavior of these tiny particles may be more finely tunable than that of dyes and, thus, may offer a promising way to solve some vexing problems associated with biological labeling. (W. Chan, D. J. Maxwell, X. Gao, R. E. Bailey, M. Y. Han, and S. M. Nie, Luminescent quantum dots for multiplexed biological detection and imaging, Current Opinion in Biotechnology, 13, 40-46 (2002) the entire contents of which are hereby expressly incorporated by reference in their entirety.)

The chemical synthesis of nanoparticles is typically achieved by a single reaction involving a chemical transformation of a precursor source of inorganic material followed by a nanocrystallization process, in the same vessel. Desired and novel properties of nanoparticles can be obtained by fine control of the synthetic conditions that determine size, size distribution, emission wavelength, and surface characteristics. Thus, nanoparticle biological probes are easier and more economical to fabricate and are less expensive than most commercially available organic dyes. More importantly, the specific photochemical reactions that cause organic dyes to photobleach or to crosslink nonspecifically with biological samples are far less common for inorganic nanoparticles.

In comparison with organic dyes such as rhodamine, this new class of luminescent probes is 20 times as bright, 100 times as stable against photobleaching, and one-third as wide in spectral linewidth. Thus, inorganic nanoparticles offer tremendous application potential in biomedicine and biology and thereby have become a robust research topic. However, there is no prior report or teaching of using such nanoparticles for in vivo radiation dosimetry and dose imaging.

Scintillation Luminescence

Scintillators have many applications including radiation detection, biomedical imaging, and radiation therapy. For radiation measurement, a scintillator must emit in a suitable wavelength range, have high efficiency, have high sensitivity, have a fast or rapid response, and exhibit high transparency to the emitted light. Although there are many scintillator materials available, there currently does not exist a scintillator that provides the desired combination of stopping power (absorption coefficient), light output, and decay time.

A scintillation luminescence process can be represented as the sequence of the following stages: (1) Absorption of the ionizing radiation (X-ray photons); (2) Creation of primary electrons and holes; (3) Thermalization of the electrons (and holes) resulting in a number of electron-hole pairs (excitons or e-h pairs) with energy roughly equal to the band-gap energy $E_g$ or electron-phonon relaxation; (4) Energy transfer from the electron-hole pairs to the luminescence centers inducing their excitation; and (5) Emission from the luminescence centers. The quantum efficiency of scintillation luminescence is related to each step of the above process.

Phosphors made with high atomic number elements usually have high stopping power and a high absorption coefficient for radiation; and thus have high luminescence efficiency. For example, $BaFX:Eu^{2+}$ (X=Cl, Br and I) phosphors are efficient scintillators that have been used for X-ray intensifiers and digital imaging plate systems (A. M. Gurvich, C. Hall, I. A. Kamenskikh, I. H. Muro, V. V. Mikhilin and J. S. Worgan, Phosphors for luminescent imaging plates, Journal of X-ray science and technology, 1996, 6: 48-62 the entire contents of which are hereby expressly incorporated by reference in their entirety). The relatively long decay lifetime of $Eu^{2+}$ emission (800 ns), however, presents a challenging issue for the practical applications of these phosphors.

For a scintillator, the conversion or energy efficiency η may be expressed as $$\eta = \frac{h v_m N_{ph}}{E_r}, \quad (1)$$

where $N_{ph}$ is the total number of photons emitted upon interaction with incident radiation of higher energy ($E_r$) and $hv_m$ is the mean energy of emitted photons.

The number of created e-h pairs, $N_{eh}$, is controlled by the average energy, $\xi_{eh}$, needed for the creation of an e-h pair as described by:

$$N_{eh} = \frac{E_r}{\xi_{eh}}, \quad (2)$$

where $\xi_{eh}$ is dependent on the kind of crystal and the energy band-gap, $\xi_{eh}=\beta E_g$. β is a numerical coefficient based on the material, typically 1.5-2 for ionic crystals and 3-4 for a material with a predominantly covalent type of binding (semiconductors).

Assuming that every e-h pair produces an average of α photons ($\alpha=N_{ph}/N_{eh}$), then, $N_{ph}=\alpha N_{eh}=TqN_{eh}$. The quantity α depends on the transport/transfer efficiency of the e-h pair energy to the luminescence center (T) and the quantum efficiency (q) for the final luminescent process: $\alpha=Tq$. Generally, if the Stokes shift is smaller, the luminescence efficiency is higher. Theoretically, this is related to electron-phonon coupling. If electron-phonon coupling is weak, the Stokes shift is small, and, therefore, the scintillation luminescence efficiency will be higher. Electron-phonon coupling is weaker for smaller sized nanoparticles due to the decrease in the density of states. As a result, the Stokes shift is smaller for smaller sized particles. This indicates that SL can be enhanced in nanoparticles as a result of quantum size confinement.

The efficiency of phosphors excited by ionizing radiation depends on the energy losses of the electronic excitations during their relaxation. This process is actually related to electron-phonon or exciton-phonon coupling. In ionic crystals, electron-phonon coupling is weaker, so the thermalization energy loss is less than in semiconductors in which the electron-phonon coupling is stronger. As was stated previously, quantum size confinement weakens electron-phonon coupling as a result of energy band splitting and decreased density of the states. Hence, energy loss due to thermalization is less in nanoparticles, which enables nanoparticles to be more efficient for scintillation luminescence. Following e-h pair creation is the so-called migration stage, in which migrating electronic excitations transfer their energy to luminescence centers. This is an important component for efficient scintillation luminescence. The energy losses in the migration stage depend on spatial distribution of electrons and holes relative to luminescence centers. If electron-hole pairs created in the track are found adjacent to a luminescence center, the recombination process is effective.

In nanoparticles, due to size confinement, the spatial distribution of luminescence centers and carriers is confined within the particles, which is favorable for energy transfer from carriers to centers. Additionally, because the critical concentration of luminescence quenching in nanoparticles is higher than in corresponding bulk materials, the concentration of luminescence centers within scintillation nanoparticles can be higher than in bulk materials. The concentration of luminescent centers can be increased through greater nanoparticle dopant concentrations, which results in a decrease in the spatial distances between the luminescence centers and the carriers and, therefore, increases the probability of energy transfer from electron-hole pairs to the luminescence centers. Further, energy migration outside of nanoparticles is difficult or impossible because of high energy barriers at the surface and between the boundaries of nanoparticles. All these factors in nanoparticles are favorable for energy transfer from e-h pairs to luminescence centers.

Once the excitation energy reaches the luminescence centers, scintillation luminescence occurs. At this stage, luminescence efficiency and other properties are totally determined by the characteristics of the luminescence centers. Due to quantum size confinement and the increased overlap of electron and hole wave functions, nanoparticles have greater luminescence efficiency with shorter decay lifetimes than those of corresponding bulk materials. Taken together, these factors compellingly describe the advantages of using nanoparticles as scintillation materials. Scintillation nanoparticles, have, therefore, enhanced light output or luminescence efficiency when compared to the more traditional micron-sized scintillators.

The strong luminescence and ultra-fast decay lifetime of semiconductor nanoparticles provides a new solution to the design and fabrication of high efficiency scintillators with fast or rapid responses. The oscillator strength, f, is an important optical parameter that underlies the absorption cross-section, recombination rate, luminescence efficiency, and the radiative lifetime in materials. The oscillator strength of the free exciton is given by:

$$f_{ex} = \frac{2m}{\hbar^2} \Delta E |\mu|^2 |U(0)|^2 \qquad (3)$$

where m is the electron mass, $\Delta E$ is the transition energy, $\mu$ is the transition dipole moment, and $|U(0)|^2$ represents the probability of finding the electron and hole at the same site (the overlap factor). In nanostructured materials, the electron-hole overlap factor increases largely due to quantum size confinement, thus yielding an increase in the oscillator strength. The oscillator strength is also related to the electron-hole exchange interaction that plays a key role in determining the exciton recombination rate. In bulk semiconductors, due to the extreme delocalization of the electron or hole, the electron-hole exchange interaction term is small; while in molecule-sized nanoparticles, due to confinement, the exchange term is large. Thus, there is a large enhancement of the oscillator strength between bulk and nanostructured materials. Nanoparticles have, therefore, higher luminescence efficiencies than bulk materials.

The natural lifetime of a transition is related to the absorption cross section or oscillator strength f by $$\tau = 4.5(\lambda_A^2/nf) \qquad (4)$$

where n is the refractive index and $\lambda_A$ is the emission wavelength. Thus, a strong transition has a large radiative rate and therefore a short natural lifetime. Semiconductor quantum sized nanoparticles, therefore provide for a promising new radiation detection material with shorter lifetimes.

The stopping power of most semiconductors is low, however, leading to a weak scintillation luminescence. In the presently disclosed and claimed invention, we demonstrate the enhancement of nanoparticle scintillation luminescence by encapsulation of nanoparticles in $BaFX:Eu^{2+}$ phosphors. The intense X-ray luminescence observed from CdTe nanoparticles in $BaFBr:Eu^{2+}$ phosphors indicates that these nanocomposite materials do provide a new type of efficient scintillator.

Scintillation Luminescence for Dosimetry

Radiation hardness is a term that is generally applied to the measure of the maximum dose a scintillator can tolerate without damage. Radiation can create defects and color centers or change the state of luminescence centers, such as valence states, in scintillators. These changes in turn affect the luminescence of the scintillator. Consequently, the scintillation luminescence intensity/energy will be relative to the radiation dosage in a certain dose range. By taking advantage of the variation of the luminescence intensity/energy upon radiation exposure, a dosimeter may be fabricated from SL nanoparticles. One phenomenon that should be noted is that some heavy crystals irradiated by high energy rays may themselves generate secondary radioactivity. This may influence the operation of the dosimeter and, more importantly, if not accounted for the additional radiation may be harmful. Thus, it is desirable to work with dosimetry systems based on those nanoparticles that do not present such risks.

Scintillator single crystals or thin films are widely used for nuclear radiation detection and medical imaging. (C. W. E. van Eijk, Inorganic scintillators in medical imaging, Physics in Medicine and Biology, 2002, 47: R85-R106, the entire contents of which are hereby expressly incorporated by reference in their entirety). In these applications the scintillators are required to have high stability. Some scintillators can tolerate high doses of radiation with high stability, while some are more sensitive to the radiation dose. Most scintillators, to a greater or lesser extent, change their intensity or emission energies upon exposure to radiation. In traditional applications for radiation detection and imaging, scintillators sensitive to radiation have generally been treated as poor phosphors and were not considered for further investigation or application. In the presently disclosed and claimed inventions, the radiation sensitivity of scintillation nanoparticles is used as the cornerstone for the design and fabrication of a new system for radiation dose imaging and dosimetry.

For intrinsic scintillators, the quenching of luminescence by ionizing radiation primarily results from the creation of defects or color centers. Once these defects or color centers are formed, they can compete with the luminescence centers (excitons) for carriers, re-absorb the emitted light, and decrease the transmission of the crystals, all of which can result in quenching of luminescence. The presence of defects or color centers in crystals can also vary the environments (symmetry and chemical bonds) of the luminescence centers; hence, the emission wavelength is also changed with increases in radiation dose.

Color centers play an important role in optical dosimetries such as thermoluminescence (TL) dosimetry and photo-stimulated luminescence (PSL) dosimetry. TL is a recombination luminescence that results from "bleaching" the color centers by heating while PSL is produced by exposure to light. Since the concentration of color centers formed in the crystals is proportional to radiation dosage, the TL or PSL intensity is proportional to the formation of color centers which is, in turn, proportional to the amount of radiation exposure. This is the working principle behind TL and PSL dosimeters.

TL and PSL dosimeters require a second excitation energy (PSL requires light or TL requires heat), however, to produce a reading. For SL dosimetry, the radiation beam itself serves as the luminescence excitation. Therefore, the operation of scintillation dosimetry as presently disclosed and claimed herein, is much simpler and significantly more economical than other optical dosimeters. An additional advantage of scintillation dosimeters is the ability to obtain real-time radiation dosage measurements.

Dose Dependent Scintillation Luminescence from Doped Phosphors

For doped phosphors, the interaction with radiation is more complex. In addition to the generation of defects or color centers, oxidation or reduction of the dopants can occur. For example, in $Eu^{3+}$ and $Tb^{3+}$ co-doped phosphors, upon irradiation, $Eu^{3+}$ is reduced while $Tb^{3+}$ is oxidized—thus, $Tb^{3+}+Eu^{3+}\rightarrow Tb^{4+}+Eu^{2+}$. Oxidation or reduction of rare earth (RE) elements is determined by the oxidation or reduction potentials of the ions. The reaction can also be explained by considering the conjugate electronic configuration ions. The two conjugate electronic configuration ions will exchange one electron in order to reach a more stable configuration when fully filled ($4f^{14}$, $4f^0$) or half-filled ($4f^7$). A good example of conjugate electronic configuration ions is $Eu^{3+}(4f^6)$ and $Tb^{3+}$ ($4f^8$). When they are co-doped in the same host, one electron will transfer from $Tb^{3+}$ to $Eu^{3+}$ and both ions will assume the more stable $4f^7$ configuration as in:

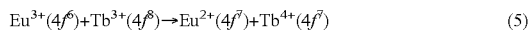

$$Eu^{3+}(4f^6)+Tb^{3+}(4f^8)\rightarrow Eu^{2+}(4f^7)+Tb^{4+}(4f^7) \qquad (5)$$

This charge transfer reaction can be used for radiation measurement as part of the nanoparticle dosimetry methods described and claimed herein.

Strong X-ray scintillation luminescence is observed from $ZnS:Mn^{2+}$; $ZnS:Mn^{2+},Yb^{3+}$; $Y_2O_3:Eu^{3+}$; $BaFBr:Eu^{2+}$; $BaFBr:Tb^{3+}$; and $YF_3:Tb^{3+}$ nanoparticles. For BaFBr phosphors in powder form co-doped with $Eu^{2+}$ (2%) and I (1%), the emission of $Eu^{2+}$ increases in intensity with X-ray irradiation time, as shown in FIG. 1.

Figure 2:
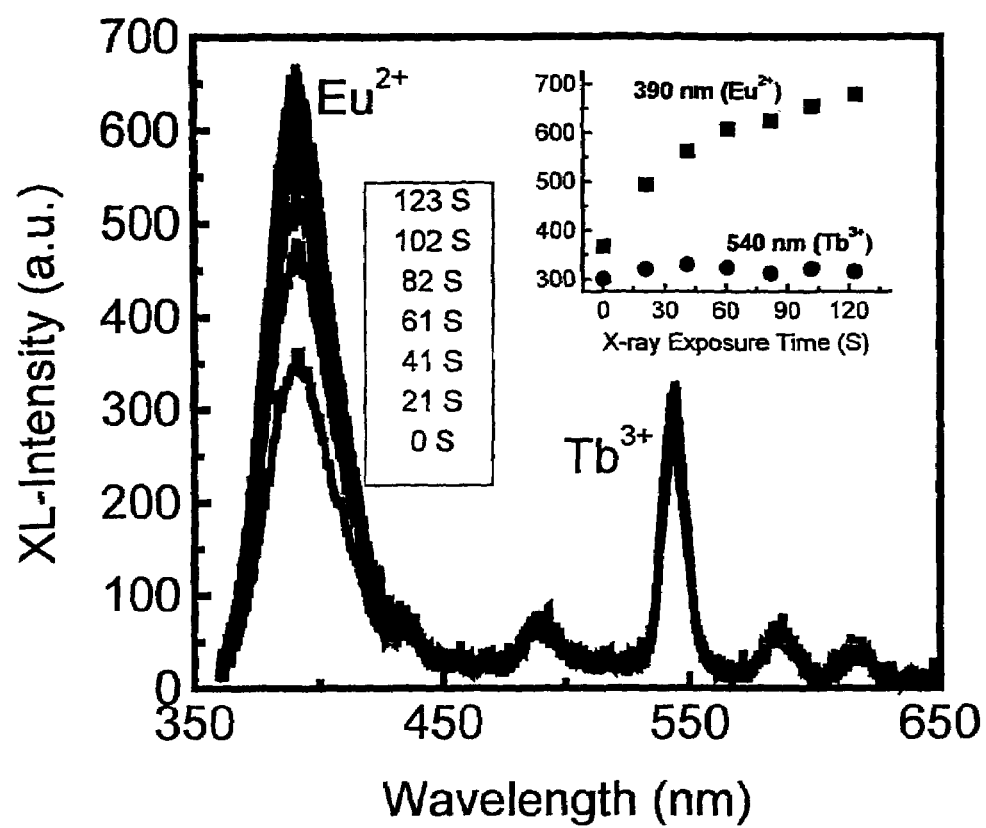
FIG. 2 shows the X-ray excited emission spectra of the BaFBr:$Eu^{2+}$, I, $Tb^{3+}$ (2%, 1%, 2%) thin film after X-ray irradiation at 0, 21, 41, 61, 82, 102, and 123 s. The inset shows the intensities of the $Eu^{2+}$ emission at 390 nm and the $Tb^{3+}$ emission at 540 nm as a function of X-ray exposure time.
Figure 3:
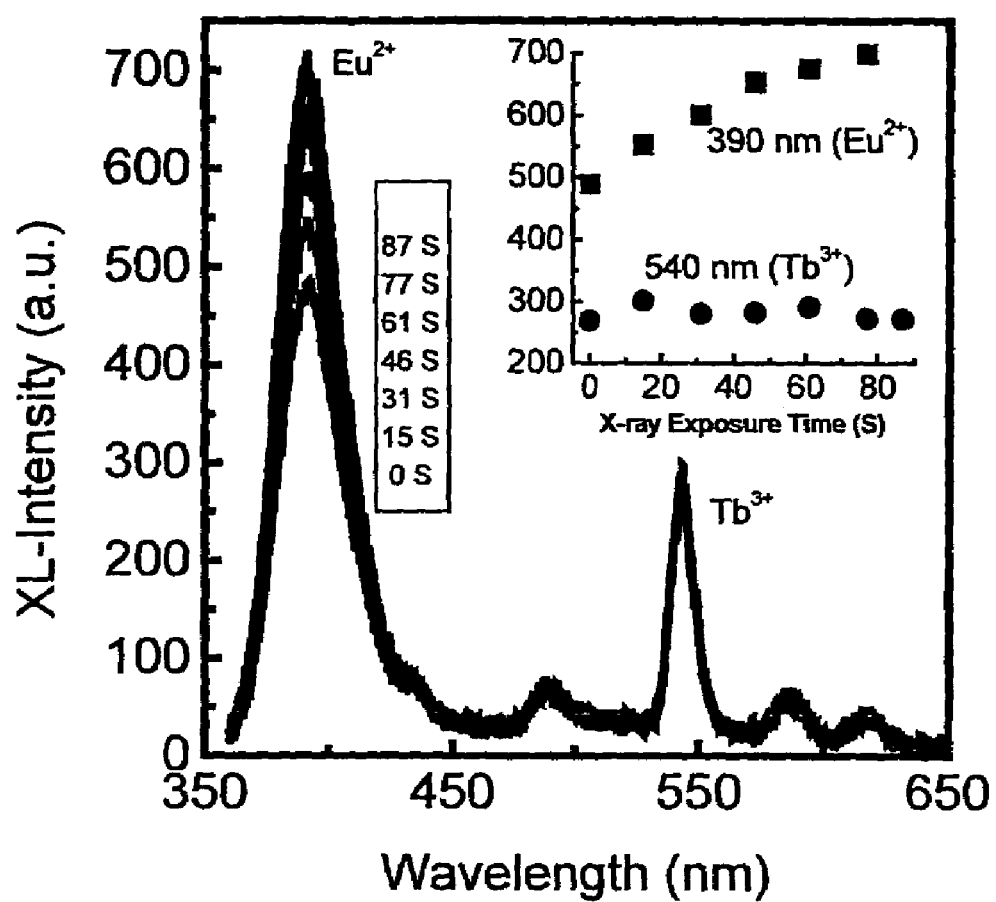
FIG. 3 shows the X-ray excited emission spectra of the BaFBr:$Eu^{2+}$, I, $Tb^{3+}$ (8%) thin film after X-ray irradiation at 0, 15, 31, 46, 61, 77, and 87 s. The inset shows the intensities of the $Eu^{2+}$ emission at 390 nm and the $Tb^{3+}$ emission at 540 nm as a function of X-ray exposure time.

Compressed pellets were prepared from the powders and used as targets for pulsed laser deposition (PLD). In PLD, an energetic, short pulse laser is used to excite material from a target such that the material forms a thin film on a substrate. PLD can retain the nanoparticle size and may, in some circumstances, improve the material's phase purity. For the $BaFBr:Eu^{2+}$, I, $Tb^{3+}$ co-doped phosphor, the emission intensity of $Eu^{2+}$ increases while that of $Tb^{3+}$ remains almost constant with increasing X-ray dose. The X-ray excited emission spectra of the $BaFBr:Eu^{2+}$, I, $Tb^{3+}$ (2%) thin film after X-ray irradiation at 0, 21, 41, 61, 82, 102, and 123 s is shown in FIG. 2. The inset shows the intensities of the $Eu^{2+}$ emission at 390 nm and the $Tb^{3+}$ emission at 540 nm as a function of X-ray exposure time. For increased Tb doping, the X-ray excited emission spectra of the $BaFBr:Eu^{2+}$, I, $Tb^{3+}$ (8%) thin film after X-ray irradiation at 0, 15, 31, 46, 61, 77, and 87 s is shown in FIG. 3. The inset shows the intensities of the $Eu^{2+}$ emission at 390 nm and the $Tb^{3+}$ emission at 540 nm as a function of X-ray exposure time.

For these films, the emission from $Tb^{3+}$ is approximately constant while the emission from $Eu^{2+}$ increases with the total radiation dose, giving a close to linear change in peak ratio. The measurement of peak ratio is much easier and more reliable than a single peak intensity measurement in practical applications. The advantage of ratio measurements for improved reliability is that variations of the optical path, such as the bend of an optical fiber or diffraction with skin penetration, can easily change the detected fluorescence intensity, whereas the ratio of the two peak intensities is much less dependent on such factors.

Figure 4:
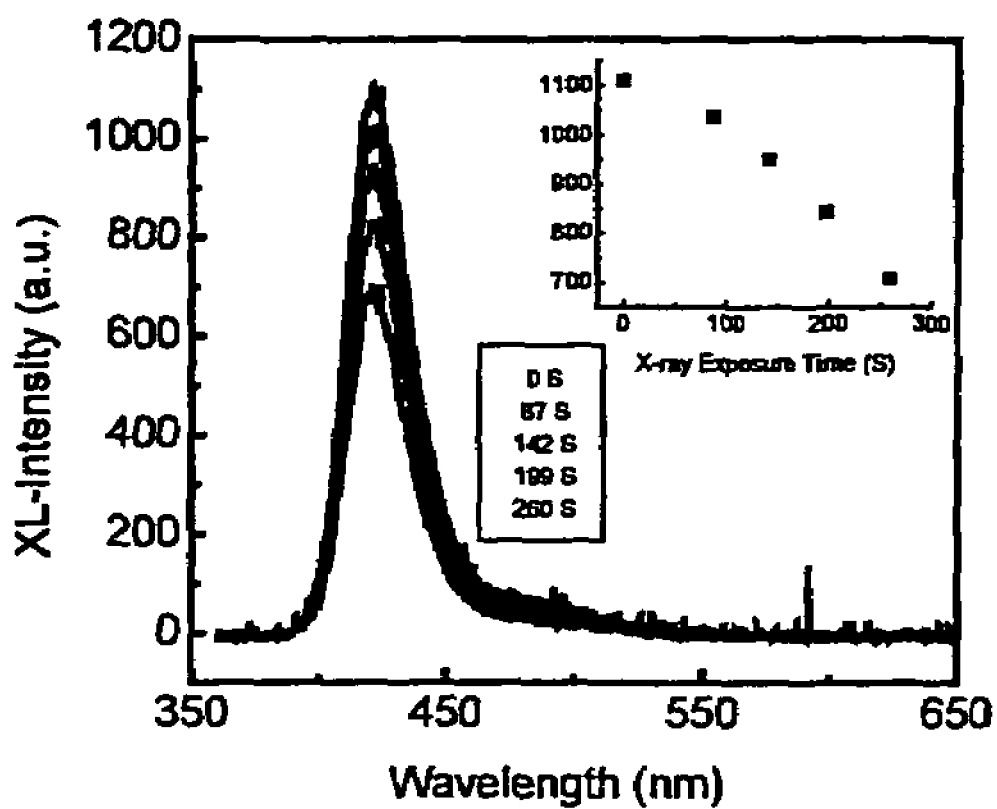
FIG. 4 shows the X-ray excited luminescence spectra of a $EuCl_2$ phosphor in Zeolite-Y after X-ray irradiation at 0, 87, 142, 199, and 260 s. The inset shows the intensity of the $Eu^{2+}$ emission at 400 nm as a function of X-ray exposure time.

In FIG. 4, the X-ray excited luminescence from an $EuCl_2$ phosphor prepared in the nanometer-sized pores of zeolite-Y is shown. Initially, there were only $Eu^{2+}$ ions and no $Eu^{3+}$ ions in this phosphor. The emission near 400 nm is from the $Eu^{2+}$ ions and decreases with radiation dose. The accepted model for this is that some of the $Eu^{2+}$ ions are converted to $Eu^{3+}$ ions.

Figure 5:
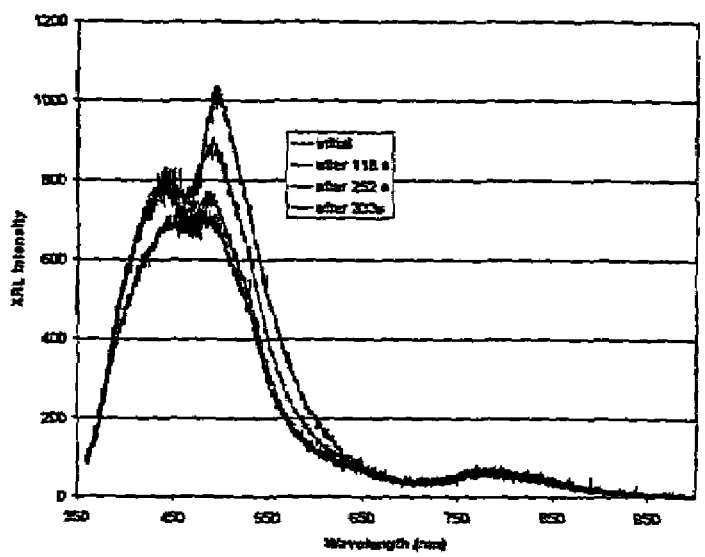
FIG. 5 shows the X-ray excited luminescence spectra of BaFBr co-doped with Ce and Tb after increasing radiation time.

For BaFBr co-doped with Ce and Tb, two peaks are seen. Initially, there is a peak at 493 nm with a shoulder near 442 nm. As the radiation time increases, the 493 nm peak decreases and the 442 nm peak increases as shown in FIG. 5.

Figure 6:
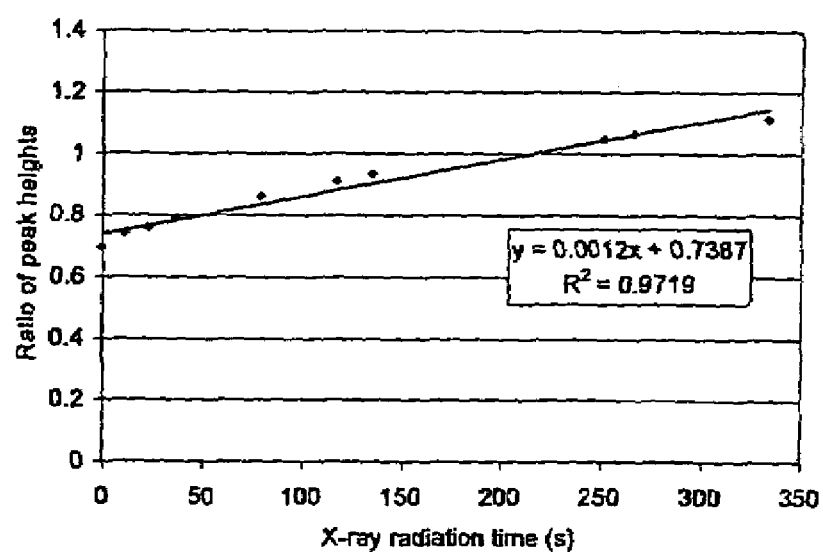
FIG. 6 shows the ratio of the 442 nm peak height to the 493 nm peak height for BaFBr co-doped with Ce and Tb as irradiation time (and total dose) increases.

FIG. 6 shows the change in peak ratio over radiation time. The linear fit to this data is shown in the inset box.

Figure 7:
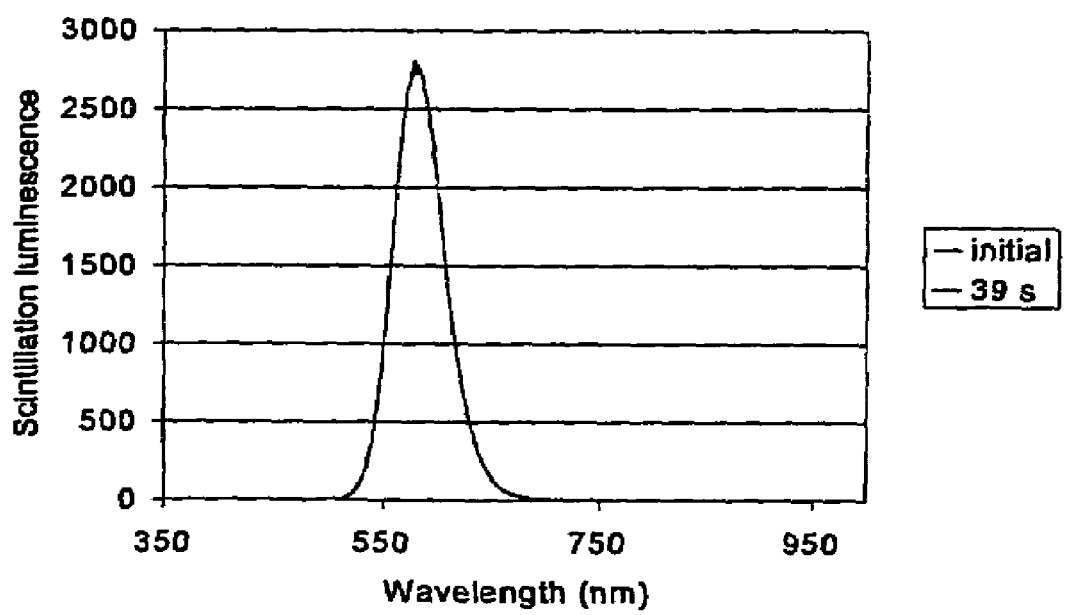
FIG. 7 shows the X-ray excited luminescence spectra of ZnMgS nanoparticles doped with 1% $Mn^{2+}$.
Figure 8:
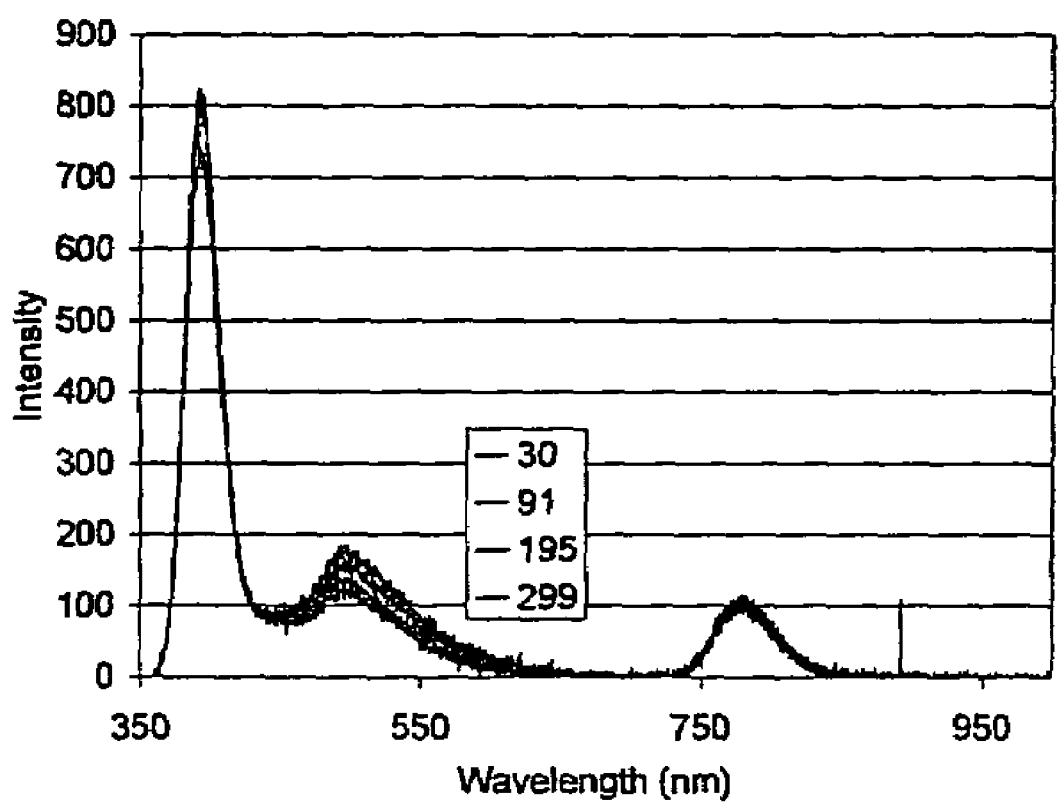
FIG. 8 shows the X-ray excited luminescence spectra of BaFBr nanoparticles doped with Mn, Ce, and Eu.

For $Mn^{2+}$ as a dopant, a red scintillation luminescence is expected. From ZnMgS nanoparticles doped with 1% $Mn^{2+}$, strong scintillation luminescence was observed. This luminescence did not, however, change over the 40 seconds of observation, as shown in FIG. 7 (the two spectra are indistinguishable). From ZnS doped with Mn and Yb, a single SL peak at 605 nm was observed. For BaFBr doped with Mn, Ce, and Eu, there are multiple peaks. There is an initial increase in the SL peak at 390 nm, but after that it stabilized, while the peak at 500 nm continued to decrease linearly with X-ray radiation time, as shown in FIG. 8.

Figure 9:
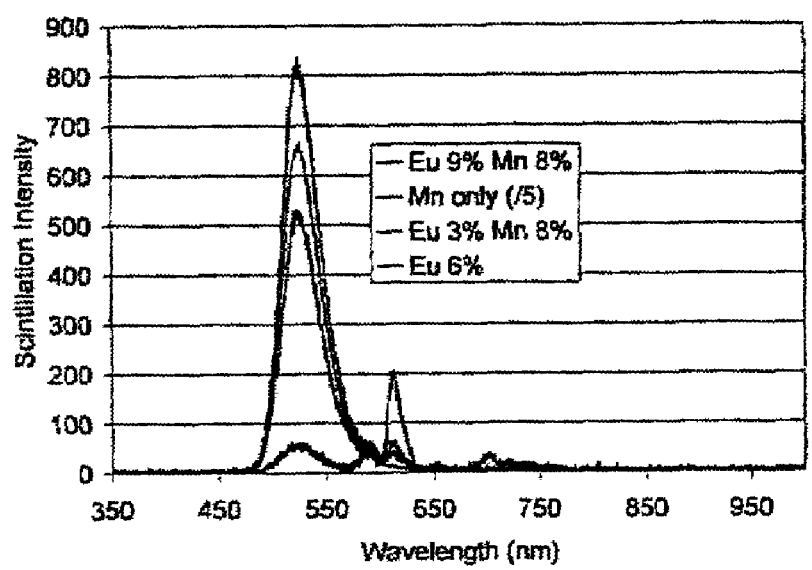
FIG. 9 shows the X-ray excited luminescence spectra of $Zn_2SiO_4$ doped with Eu and Mn ions.

Scintillation luminescence of nanoparticles of $Zn_2SiO_4$ doped with various combinations of Eu and Mn are shown in FIG. 9. Based on the above observations and experimental data, $Mn^{2+}$ ($Mn^{2+}\rightarrow Mn^{3+}$), $Cr^{3+}$ ($Cr^{3+}\rightarrow Cr^{4+}$), $Nd^{3+}$ ($Nd^{3+}\rightarrow Nd^{4+}$), $Eu^{2+}$ and $Eu^{3+}$ ($Eu^{2+}\leftrightarrows Eu^{3+}$), $Yb^{3+}$ ($Yb^{3+}\rightarrow Yb^{2+}$), and $Pr^{3+}$ ($Pr^{3+}\rightarrow Pr^{4+}$) are expected to be good dopant candidates for doped scintillation nanoparticles. In selecting these dopant candidates, primary consideration was given to their emission wavelengths. All of these ions have emission wavelengths in the 700-1200 nm range or have emission wavelengths that can be adjusted to this range by choosing hosts with suitable crystal fields.

Advantages of Scintillation Nanoparticles for In Vivo Dosimetry and Imaging

Dose imaging and dosimeter materials can be designed and fabricated by directly using the scintillation luminescence of nanoparticle scintillators. This novel type of dosimetry using nanoparticle scintillators has the following advantages: (1) Simultaneous in vivo detection, dose imaging, and dose measurement; (2) in vivo or in situ detection that is more reliable and more accurate than current methods; (3) Emissions of 700-1200 nm that will penetrate tissue making in vivo detection feasible; (4) Excitation directly by ionizing radiation, thereby eliminating any extra light source or optical fiber and hence making SL-based dosimetry both simpler and more economical; (5) By judicious design of the nanoparticles, applications for temperature sensing, oxygen-dosimetry, and contrast imaging are also possible; and (6) Nanoparticles can specifically target organs or tumors and, thus, these particles can be used to deliver proteins, drugs or oligonucleotides for treatment (gene therapy, clot dissolution, eradicators of xenobiotics, drugs which improve the effectiveness of radiation therapy, etc.).

For in vivo imaging and dosimetry applications, an efficient scintillator material must meet requirements in addition to high conversion efficiency and scintillation light yield in order to be commercially practical and useful. Such additional requirements include properties such as decay time or duration of the scintillation light pulse, level of afterglow (phosphorescence), temperature stability, chemical stability, transmission and index of refraction, radiation hardness, density, emission wavelength, and proportionality between effectiveness and cost. The nanoparticles should also be stable in a biological environment, water soluble, and biocompatible with little-or-no toxicity. Because light emitted at wavelengths between 700 and 1200 nm has the greatest transmission through tissue, the materials' emission wavelengths should also fall in this range. For dosimetry, the scintillation luminescence should have a linear or close-to-linear relationship between the luminescence intensity/energy and radiation dosage. Additionally, for potential applications in X-ray imaging, the particles should have high scintillation luminescence with fast or rapid response times and short or no afterglow. These are the primary considerations that must be taken into account when designing scintillation nanoparticles for in vivo radiation imaging and dosimetry.

In vivo detection requires that the nanoparticles be biocompatible. Many semiconductor nanoparticles have, however, a real potential for toxicity. All potential uses of nanoparticles in biology and biomedicine (especially those that require insertion of nanoparticles into living tissue) face such an obstacle. One solution to this problem resides in devising means of coating the nanoparticles with biocompatible materials, such as silica, titanium dioxide, zinc oxide, certain polymers (such as polyethylene glycol), or proteins. Many of these approaches are well known in the art (Y. Zhang, N. Kohler, M. Zhang, Surface modification of superparamagnetic magnetite nanoparticles and their intracellular uptake, Biomaterials 23, 1553-1561 (2002) and M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497, the entire contents of which are hereby expressly incorporated by reference in their entirety.) Another approach is to use non-toxic materials as precursors. In order to effectively transport the nanoparticles to the target organ or tissue, immunogenic, antigenic, and non-specific binding of the nanoparticles must be minimized.

An effective approach to solve these problems is to further modify the surface of nanoparticles with low protein-binding molecules such as poly(ethylene glycol) (PEG), which is a widely used biocompatible coating. PEG coated magnetite nanoparticles were reported to be biocompatible and can be internalized by cancer cells. (Y. Zhang, N. Kohler, M. Zhang, Surface modification of superparamagnetic magnetite nanoparticles and their intracellular uptake, Biomaterials 23, 1553-1561 (2002) the entire contents of which are hereby expressly incorporated by reference in their entirety.) This can be done by using PEG derivatives as stabilizers during synthesis or by performing post-synthesis modification. In addition, biocompatibility of nanoparticles can be improved by coating the nanoparticles with proteins, such as bovine serum albumin (BSA). It is also important that the materials produce SL not just in powder form, but in solution as well as in biological environments. Coatings can also improve SL in solution. For example, silica coated semiconductor nanoparticles have strong and stable luminescence in water. (M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497, the entire contents of which are hereby expressly incorporated by reference in their entirety.)

Figure 10:
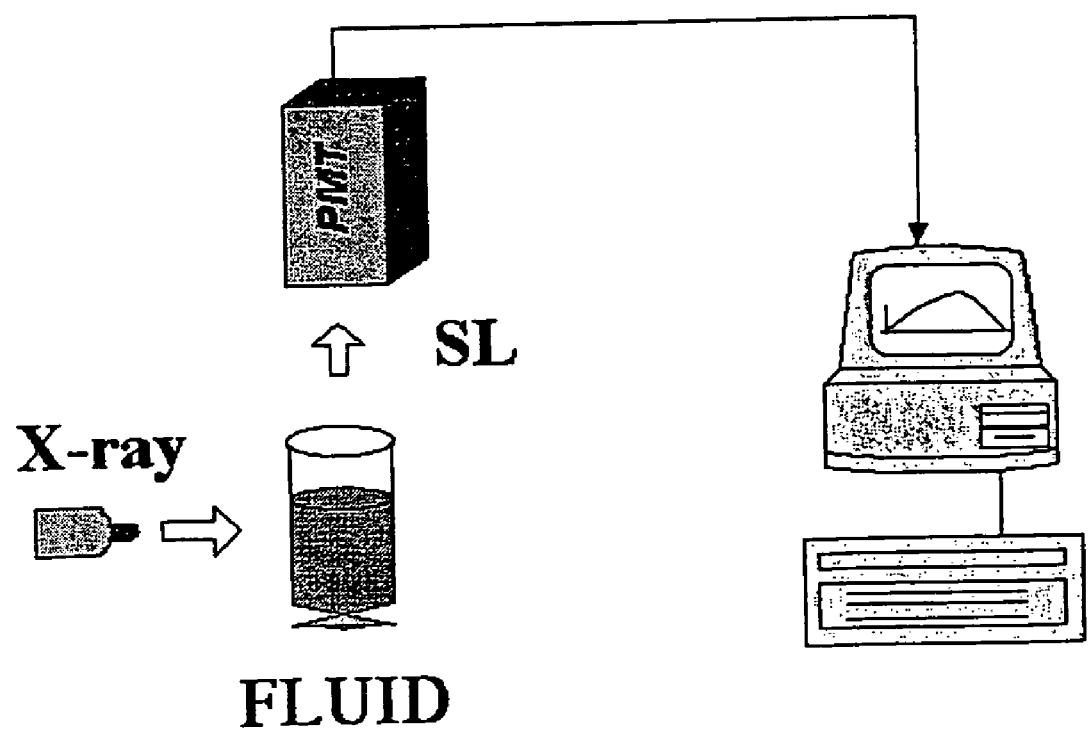
FIG. 10 shows a schematic illustration for measurement of X-ray excited scintillation luminescence (SL) from nanoparticle solution (fluid).

One such method for measuring the properties of scintillation luminescence from nanoparticles in solution and in biological environments is schematically shown in FIG. 10. Generally, phosphors lose their luminescence when they are in water solution. The luminescence quenching in solution is due to energy migration through the vibrational energy levels of water. For nanoparticles, however, the situation is quite different. Most nanoparticles such as CdTe and $ZnS:Mn^{2+}$ remain strongly luminescent in aqueous solution. The mechanism for nanoparticle luminescence in solution is not yet fully understood, but it is believed that stabilizer and coating layers of such nanoparticles is indicated. The coating layer of nanoparticles may stop energy migration from the nanoparticles (the emitters) to water and, thus, the water is not able to quench their luminescence. It is for this reason that the presently disclosed and claimed inventions utilize luminescent nanoparticles for in vivo radiation dosimetry.

Another major obstacle to the use of nanoparticles for in vivo radiation dosimetry is the need to sense the light that is produced in response to the radiation. As noted earlier, the best approach to overcome this obstacle is the use of materials that emit in the 700-1200 nm range. Thus, the selection of materials must specifically address issues such as biocompatibility while also taking into consideration emission wavelengths as deployed—that is, with coatings or other strategies that promote the usability of the nanoparticles for in vivo applications. Because the light output of the SL will be related to the depth, the color, location, and tissue make-up of the tumor, as well as the age, gender, and other physiological traits of patients, characterization of the response is required. Approaches such as monitoring changes in peak ratios that limit these variations are preferred.

Selection of Nanoparticles

Classical scintillators can be divided into four material groups: halides, oxides, chalcogenides, and glasses. Traditionally, thin films or crystals of these materials were used for nuclear radiation detection in the laboratory. In the presently disclosed and claimed inventions, scintillators are used for a new and special application: in vivo detection of radiation. To meet these requirements, three types of nanoparticles have been identified that are fully capable of functioning as scintillators in biological environments, namely semiconductor nanoparticles; doped nanoparticles; and encapsulated nanoparticles.

Semiconductor Nanoparticles

Luminescent nanoparticles (such as ZnO, ZnS, CdS, ZnSe, CdSe, CdTe, Si, InP, and InAs) have been studied extensively and have very well documented preparation methods, as well as extensive characterization of their luminescence and related properties. However, the energy gaps of ZnO, ZnS, CdS, and ZnSe are 3.44 eV (360 nm), 3.68 eV (336 nm), 2.49 eV (497.6 nm), and 2.7 eV (459 nm), respectively. Band-to-band emissions from these nanoparticles are in the ultraviolet to visible range. Therefore, they are not suitable for in vivo detection, although they may be suited for other applications.

The energy gap of InAs is 0.36 eV and its emission wavelength (3441 nm) is much longer than is required for a nanoparticle scintillation in vivo dosimeter. The energy gap of InP is 1.35 eV. The emission wavelengths of InP nanoparticles are from 800 nm to 1550 nm. The chemical compounds for making InP and InAs nanoparticles are, however, explosive upon contact with air. An oxygen-free system is required for making such nanoparticles. Therefore, InP and InAs are not preferred nanoparticles for use with the presently disclosed and claimed inventions. The energy gaps of CdTe, CdSe, PbSe, and Si are 1.43 eV (866 nm), 1.75 eV (708 nm), 1.23 eV (1007 nm) and 1.11 eV (1116 nm), respectively, which makes these nanoparticles well suited for in vivo applications. PbS and PbTe nanoparticles may also be suitable. Most reported CdTe and CdSe nanoparticles exhibit emission in the green to red wavelengths, however, as a result of quantum size confinement. In order to adjust the emission to 700-1200 nm, one approach that can be used is to make CdTe/CdSe and CdSe/CdS core/shell structured nanoparticles. Compared with CdTe or CdSe nanoparticles, the absorption and emission spectra of CdTe/CdSe and CdSe/CdS core/shell structures shift to longer wavelengths (X. G. Peng, M. C. Schlamp, A. V. Kadavanich and A. P. Alivisatos, J. Am. Chem. Soc., 119, 7019 (1997) the entire contents of which are explicitly incorporated herein by reference). For a 4 nm sized CdSe particle, the red shift is ~25 nm if a CdSe/CdS core/shell structured nanoparticle is formed. This red shift is predominantly a result of mixing between the core and shell LUMOs in the molecular orbital model and the loss of quantum confinement in the particle-in-a-box model (due to a bigger box). Based on the particle-in-a-box model, if the diameter of the core is 10 nm, the emission wavelength of CdTe/CdSe is at 850 nm, which is well suited for in vivo detection. Furthermore, the luminescence quantum efficiency of CdTe/CdSe can be improved by the formation of a core/shell structure due to the confinement of holes to the core. All of this indicates that core/shell structured nanoparticles are suitable for biomedical applications.

Doped Nanoparticles

An additional strategy for making suitable nanoparticles for use in the nanoparticle scintillation dosimeters disclosed and claimed herein is by doping. In doped nanoparticles, fluorescence is mainly from the dopants (emitters). Therefore, the transition properties of the dopants are very important. The emission efficiency and wavelength are influenced, however, by quantum size confinement. As with excitonic luminescence in semiconductor nanoparticles, luminescence of doped nanoparticles can also be improved by quantum size confinement both in efficiency and emission energy. Emitters chosen for doping include: $Nd^{3+}$, $Pr^{3+}$, $Yb^{3+}$, $Cr^{3+}$, $Mn^{2+}$, and $Eu^{2+}$. Absorption and emission of rare earth ions such as $Nd^{3+}$, $Pr^{3+}$, and $Yb^{3+}$ are due to f-f transitions. Because of the shielding of f electrons, f-f transitions are extremely insensitive to their environment and have high thermal stability. These emissions hardly vary in peak position even in different hosts or in different sized nanoparticles. The emission wavelengths from $Nd^{3+}$, $Yb^{3+}$, and $Pr^{3+}$ are suitable for the applications described here.

$Mn^{2+}$, $Eu^{2+}$, and $Cr^{3+}$ are efficient emitters with strong luminescence from d-d ($Mn^{2+}$, $Cr^{3+}$) or f-d ($Eu^{2+}$) transitions. The emission wavelengths of these transitions are mainly determined by the crystal field of their hosts while their quantum efficiency is mainly determined by the energy transfer from the host, which is closely related to the interaction (orbital hybridization) with the hosts. Unlike f-f transitions, d-d or f-d transitions are sensitive to their environment and their energies are quite different for various hosts. Based on our observations, the emission wavelengths of $Mn^{2+}$, $Eu^{2+}$, and $Cr^{3+}$ are not sensitive to particle sizes while their emission efficiencies can be enhanced by quantum size confinement.

Figure 11:
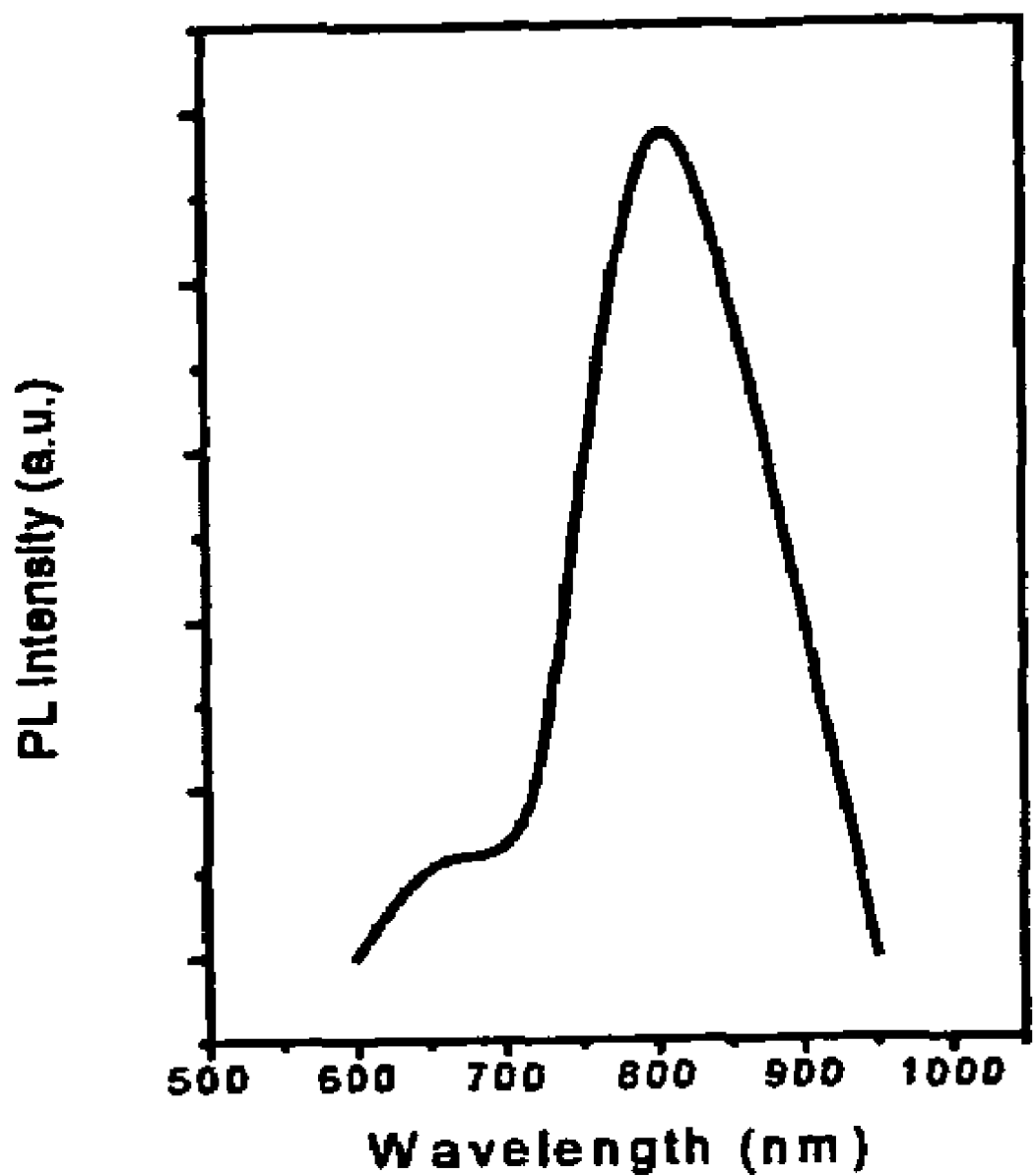
FIG. 11 shows the emission spectrum of $Mn^{2+}$ in CdTe crystal.

FIG. 11 shows the emission spectra for $Mn^{2+}$ doped in CdTe. The luminescence wavelengths are within the water window of tissue (i.e., 700-1200 nm). Thus, the doped nanoparticles of FIG. 11 are good candidates for biomedical applications. In the selection of doped nanoparticles for scintillation luminescence dosimetry, in addition to their emission wavelengths, we also need to consider the luminescence dependence on radiation dosage. The regular variation of the dopant valence states with radiation dosage makes them sensitive to radiation dosage.

Many semiconductor and insulator nanoparticles can be used as the host. A general way of describing these hosts and, more specifically, those based upon group VI elements is $M_{1-z}N_z)_{1-x}A_{1-y}B_y$ where M=Zn, Cd, Hg, Pb, Ca, Ba, Sr, and Mg; N=Zn, Cd, Hg, Pb, Ca, Ba, Sr, and Mg; A=S, Se, Te, and O; B=S, Se, Te, and O, wherein $0 \leq x < 1$, $0 < y \leq 1$, $0 < z \leq 1$. Other hosts such as $TiO_2$, $Y_2O_3$, $CaF_2$, and $Zn_2SiO_4$ are also possible, some of which have been demonstrated in the examples. Specific examples of doped nanoparticles include: $ZnS:Cr^{3+}$; $ZnS:Nd^{3+}$; $TiO_2:Nd^{3+}$; $Y_2O_3:Nd^{3+}$; $Y_2O_3:Nd^{3+}$, $Tb^{3+}$; $CdTe:Mn^{2+}$; $MS:Eu^{2+}$ (M=Ca, Sr, and Ba); $CaF_2$: $Mn^{2+}$; $CaF_2:Eu^{2+}$; $CaF_2:Nd^{3+}$; $BaFBr:Eu^{2+}$; $BaFBr:Eu^{2+}$, $Tb^{3+}$; $BaFBr:Ce^{3+}, Tb^{3+}$; $Zn_2SiO_4:Eu^{2+}$, $Mn^{2+}$; $Zn_xMg_{1-x}S$: $Mn^{2+}$ ($0 \leq x \leq 1$).

Encapsulated Nanoparticles for Scintillation Luminescence and Dosimetry

Semiconductor nanoparticles, such as CdTe, may have high photoluminescence efficiency, but low stopping power. These materials can be encapsulated by a material with good stopping power, such as $BaFX:Eu^{2+}$ (X=Cl, Br and I) phosphors. It is well known that the emission of $Eu^{2+}$ in BaFX: $Eu^{2+}$ phosphors is sensitive to radiation dose; as a result, the emission of the CdTe nanoparticles from the energy transfer from $Eu^{2+}$ ions is also dose-dependent as observed. Furthermore, the emission of semiconductor nanoparticles is size-dependent and can emit in the near-infrared range (700-1200 nm) which is the tissue optical window for in vivo imaging. Therefore, these energy-transfer semiconductor/phosphor nanocomposite materials show potential for use in radiation detection and dosimetry.

X-ray luminescence from CdTe nanoparticles is observed in $CdTe/BaFBr:Eu^{2+}$ nanocomposites while no X-ray luminescence is observed in pure CdTe nanoparticles or CdTe nanoparticles encapsulated in a BaFBr host. The energy transfer from the $Eu^{2+}$ ions to the CdTe nanoparticles is believed to be the main mechanism responsible for the X-ray luminescence of CdTe nanoparticles encapsulated in BaFBr: $Eu^{2+}$ phosphors. The sensitivity of these energy-transfer nanocomposite materials may allow their use as a new type of dosimeter for both in vitro and in vivo applications.

The general approach of encapsulating a nanoparticle in a material with a high X-ray absorption coefficient (stopping power) and the ability to transfer energy to the nanoparticle, provides the advantages of efficient emission at selectable wavelengths and also provides for a faster or more rapid response (i.e., a decrease in decay lifetime). For example, CdTe nanoparticles of different sizes have a shift in the emission wavelength. Replacing the CdTe nanoparticles with CdS, CdSe, ZnS or other II-VI semiconductors is a second method of changing the emission wavelength. A general way of describing these semiconductors is $(M_{1-z}N_z)_{1-x}A_{1-y}B_y$, where M=Zn, Cd, Hg, Pb, Ca, Ba, Sr, and Mg; N=Zn, Cd, Hg, Pb, Ca, Ba, Sr, and Mg; A=S, Se, Te, and O; B=S, Se, Te, and O, wherein $0 \leq x < 1$, $0 < y \leq 1$, $0 < z \leq 1$. A third method of changing emission wavelength is to use doped semiconductors, such as CdTe:Hg or CdTe:Mn (where CdTe:Hg refers to a semiconductor nanoparticle with a host, or majority composition, of CdTe with some percentage of the Cd replaced by Hg, a dopant). Transition metal ions, rare earth ions, and halides may all make suitable dopants. Other host material semiconductors are also useful, such as oxides (ZnO, $Y_2O_3$) or $Zn_2SiO_4$.

The encapsulating material with high stopping power can also be one of several different materials. The $BaFX:Eu^{2+}$ (X=Cl, Br and I) family has already been discussed hereinabove, but it is important to note that F and X may be present in ratios other than 1:1 and that $BaF_2$ and $BaX_2$ may also be suitable encapsulating materials. In addition to the two halides given in this formula, a third or fourth halide may also be in the composition. Other elements (such as oxygen) may also be present as dopants in the encapsulating material. The $Eu^{2+}$ might be replaced, in whole or in part, by other rare earth dopants or transition metal dopants. Similar materials such as CaFX or $CaF_2$ are also to be considered as encapsulating materials with lower toxicity than BaFX. This family of materials can be represented as $AB_xC_{2-x}$ where A is Ba, Sr, or Ca; B is F, Cl, Br, or I; C is F, Cl, Br, or I, and $0 \leq x \leq 2$.

Another approach to limiting toxicity may require a second encapsulation of the nanocomposite with a material such as silica. Silica encapsulation of nanoparticles is well known and typically proceeds with the absorption of the organic group of an organosilane molecule on the nanoparticle followed by reaction with a silica precursor such as tetraethyl orthosilicate or sodium silicate. Other encapsulation materials such as polymers (particularly polyethylene glycol) are also to be considered for use.

In one application, undoped BaFBr is used as the host, with an intrinsic emission at 400-500 nm. This overlaps with the absorption of CdTe:Hg nanoparticles. Direct energy transfer from the BaFBr to the CdTe:Hg might be significantly faster than the energy transfer through the $Eu^{2+}$ of $BaFBr:Eu^{2+}$. Faster energy transfer and faster response are one advantage of this system. A second advantage is that CdTe:Hg emits near 800 nm, which is in the near-infrared wavelength range of the tissue optical window for in vivo imaging.

Thus, three preferred nanoparticle types are: (1) Pure semiconductor nanoparticles: Si, PbSe, CdTe/CdS and CdSe/CdS core-shell structures having different sizes; (2) Doped semiconductor or insulator nanoparticles: $ZnS:Cr^{3+}$, $ZnS:Nd^{3+}$, $TiO_2:Nd^{3+}$, $Y_2O_3:Nd^{3+}$, $CdTe:Mn^{2+}$, $MS:Eu^{2+}$ (M=Ca, Sr, and Ba), $CaF_2:Mn^{2+}$, $CaF_2:Eu^{2+}$, $CaF_2:Nd^{3+}$, $BaFBr:Eu^{2+}$, BaFBr:Eu,Tb; (3) Energy-transfer nanocomposites.

Toxicity, Stability, Solubility, and Silica Coating

The nanoparticles listed hereinafter have been selected based on their toxicity, stability, biocompatibility, and luminescence (intensity and wavelength). In addition, solubility, dissolution velocity, saturation solubility, adhesion properties, surface hydophilicity, and chemical reactivity with body proteins are also to be considered during the selection process. These properties are mainly related to the surface characteristics and the stabilizing layers of the nanoparticles that are adjustable by surface modification. Surface modification for functionalizing the nanoparticles for bio-conjugation and biocompatibility is very important for targeting and delivery. In addition, for a particular application such as drug delivery, the nanoparticle system should be heat-sensitive or pH-sensitive, as are some smart polymers such as hydrogels. All these issues are tunable or selectable by the nanoparticles chosen and the coatings applied thereto.

For biological applications of inorganic nanoparticles, one of the major limiting factors is their toxicity. Generally speaking, all semiconductor nanoparticles are more or less toxic. For biomedical applications, nanoparticles with toxicity as low as possible are preferred. Pure $TiO_2$ and ZnO are biocompatible. CdTe and CdSe are toxic, while ZnS, CaS, BaS, SrS and $Y_2O_3$ are less toxic. In addition, the toxicity of nanoparticles can result from their inorganic stabilizers, such as TGA, or from dopants such as $Eu^{2+}$, $Cr^{3+}$ or $Nd^{3+}$. To reduce the toxicity or to make these nanoparticles bio-inert or biocompatible, one strategy is to coat them with silica. Silica is used as a coating material in a wide range of industrial colloid products from paints and magnetic fluids to high-quality paper coatings. Furthermore, silica is chemically and biologically inert and optically transparent.

Biological applications require "water-soluble" nanoparticles. In this sense, "water-soluble" does not have the sense of "soluble" in traditional chemistry. In traditional chemistry, if a chemical such as NaCl is water soluble, it means the chemical will be dissolved as free cationic ($Na^+$) and anionic ($Cl^-$) ions. In saying that a nanoparticle is "water-soluble," we mean the nanoparticle can stay stable and suspended in water without precipitation. The solubility of nanoparticles is determined by three parameters: size, stabilization, and surface charge. Generally, the smaller the size, the higher the solubility is. In order to have water-soluble nanoparticles, the nanoparticle stabilizer must be water-soluble or hydrophilic as well. The nanoparticles must have high surface charge in order to keep them separated. If nanoparticles aggregate as clusters they will precipitate. So, in order to enable a nanoparticle to "swim" in fluids, "swings" must be fixed to them. These "swings" can be made by surface modification. Coating nanoparticles with a layer of silica has proved a successful strategy for making nanoparticles soluble in water and biocompatible. Thus, silica coating is an important and necessary procedure because it is a good approach to the biocompatibility, solubility, and stability of nanoparticles. Silica or $TiO_2$ coating has been reported to reduce the fluorescence of some nanoparticles. The quenching by silica or $TiO_2$ coating is probably due to the excitation light not penetrating through the silica or $TiO_2$ layer to the nanoparticle core. However, this is not an issue with scintillation luminescence because the attenuation length (a few micrometers) of an X-ray is longer than the coating thickness.

For in vivo applications, the nanoparticles need to be able to travel in the bloodstream, to reach the target tissue, and to be taken up by target cells. Nanoparticles have large surface area: volume ratios and tend to agglomerate and adsorb plasma proteins. When this happens, they are quickly cleared by macrophages before they can reach the target cells. In order to solve this issue, the nanoparticle surface can be coated with poly(ethylene glycol) PEG. PEG-coated surfaces are known to be biocompatible, nonimmunogenic, nonantigenic, and protein-resistant, which is because PEG has uncharged hydrophilic residues, and very high surface mobility leading to high steric exclusion. In addition, PEG can dissolve in both polar and nonpolar solvents and has high solubility in cell membranes; therefore, PEG-coated particles can cross cell membranes and ease the uptake process. PEG-coated magnetite nanoparticles have been reported as resistant to removal by macrophages and are subject to uptake by breast cancer cells (Y. Zhang, N. Kohler, M. Zhang, Surface modification of superparamagnetic magnetite nanoparticles and their intracellular uptake, Biomaterials 23, 1553-1561 (2002) the entire contents of which are hereby expressly incorporated by reference in their entirety.). In addition, bovine serum albumin (BSA) coating also can improve nanoparticle biocompatibility. The procedure for BSA-coating has recently been published. (Shaopeng Wang, Natalia Mamedova, Wei Chen, Joel Studer, and Nicholas A. Kotov, Antigen/Antibody Immunocomplex from CdTe Nanoparticle Bioconjugates, Nanoletters, 2002, 2(8): 817-822 the entire contents of which are hereby expressly incorporated by reference in their entirety.).

Scintillation Luminescence Dosimetry and Other Applications of Energy-Transfer Nanocomposites Based on observations that the X-ray excited luminescence intensity is dependent linearly on the radiation dose in a wide range of dosage, energy-transfer nanocomposite materials can be used in the fabrication of a novel dosimeter. In one embodiment, the energy-transfer nanocomposites are injected into tumors/tumor sites before X-ray radiation therapy occurs. The emission from the nanocomposite is monitored during therapy (and is easier to detect when the wavelength of emission has been shifted to longer wavelengths at which tissue is more transparent). Changes in this emission are used to determine the X-ray dosage sustained by the tumor, thus allowing the nanocomposites to serve as a real-time dosimeter (short computational delays for processing the changes in luminescence or determining spatial distribution may occur). Either a spatially integrated reading of average dose or an image of the spatial distribution of the dose is obtained thereby allowing more accurate radiation therapy to occur. Such a dosimetry method is minimally invasive (less invasive than fiber optic probes or implanted devices) and provides for a real-time measurement of X-ray dosage. The nanocomposite is an integral part of this dosimeter as it provides emission at longer wavelengths at which tissue is more transparent.

There are several applications for such energy-transfer materials:

1) Dosimetry (particularly in-vivo, real-time)
2) In vivo imaging
3) Medical X-ray imaging
4) Detection of other high energy radiation
5) X-ray imaging for security or non-destructive evaluation These nanocomposites are also useful for in vivo imaging. The nanocomposite is first treated in such a way so as to target it to a certain site in the body, for example—a tumor. Selective targeting systems can be divided into two main types, namely passive and active targeting, such as antigen-antibody targeting, receptor targeting.

Passive targeting is based on the phenomenon known as the enhanced permeability and retention (EPR) effect. EPR is a common effect in solid tumors. The enhanced vascular permeability of a solid tumor is important in the biology of the tumor, which greatly impacts the targeted delivery of macromolecular anticancer drugs.

Active targeting consists of selective delivery of agents by conjugates containing a receptor-targeting moiety, similar to antibody-antigen targeting. As an example, the nanocomposite surface could be treated to bind with folic acid. Folic acid is known to bind with folate receptors on ovarian tumors and thus the treated-nanocomposites would have a tendency to bind at ovarian tumors. Then when exposed to X-rays, the areas in which the nanocomposites had bound (the ovarian tumors) would luminesce, making their identification possible. In comparison to using radioactive labels for imaging, this technique results in a lower overall dose (because the radioactive labels stay in the body for a period of hours to days) and less radiation at organs that were not of concern (such as when the radioactive labels pass through the kidneys). Applications to cancers that are nearer the surface of the skin are likely to be more practicable for the detection of the emitted light. Such an in vivo imaging application may be combined with the dosimetry application as the presence of the nanocomposites would reveal the shape and extent of the tumor during radiation therapy.

When X-rays are used for medical imaging (or security or non-destructive evaluation), the detection of the X-rays is done by several methods. The use of a film is very common, sometimes in conjunction with a scintillator to convert the X-rays to visible light. Scintillators are also used with CCD cameras (charge-coupled device) for digital collection of images. Newer devices that directly convert X-rays to electronic signals are also known. The scintillators disclosed and claimed herein may have particular use in X-ray imaging, particularly where longer wavelength emission is desired in order to match the most sensitive wavelength range of a detector.

With either BaFX or other encapsulating materials, this approach could also be used for the detection of other high-energy radiation, including neutrons, positrons, and alpha, beta, and gamma radiation.

EXAMPLE 1

Preparation of CdSe Nanoparticles

One recipe for the synthesis of CdSe nanocrystals is given here as an example. A similar recipe is used for PbSe. Citrate-stabilized CdSe nanocrystals are prepared according to the following procedure: To 45 ml of water were added 0.05 g sodium citrate (Fluka) and 2 ml of $4 \times 10^{-2}$ M cadmium perchlorate (Aldrich). The pH was adjusted to 9.0 by 0.1 M NaOH (Alfa). The solution was bubbled with nitrogen for 10 minutes, and then 2 ml of $1 \times 10^{-2}$ M N,N-dimethylselenourea (Alfa) was added. The mixture was heated in a conventional 900-watt microwave oven for 50 seconds. In this recipe, the Cd:Se molar ratio is 4:1, which leads to CdSe nanoparticles with ~4.0 nm diameter; by increasing the Cd concentration it is possible to synthesize smaller CdSe nanoparticles.

EXAMPLE 2

Preparation of CdSe/CdS Core/Shell Nanoparticles

For the preparation of core-shell CdSe/CdS nanoparticles, the CdSe aqueous solution synthesized above was used as the initial material with thioacetamide as the sulfur source. To a given amount of the CdSe solution was added a $4 \times 10^{-2}$ M solution of thioacetamide (Alfa) in a quantity such that the molar ratio of $S_{added}:Se_{initial}$ was 1:1. For example, to 10 mL of the $4 \times 10^{-4}$ M (in Se) CdSe solution from Example 1, 0.1 mL of $4 \times 10^{-2}$ M solution of thioacetamide was added to have a molar ratio of $S_{added}:Se_{initial}$ of 1:1. The mixture was heated in a round-bottom flask under Ar flow at 70-80° C. for 24 hours. Then the solution was placed in ambient temperature to enhance its luminescence.

Citrate-stabilized CdSe nanoparticles made in this way show well-defined 1s-1s electronic transitions in their absorption spectra. The room-temperature excitonic emission of CdSe nanoparticles is weak. In the course of the preparation of core/shell nanocrystals, both absorption and luminescence spectra undergo changes. The heating induces a slight growth of CdSe nanocrystals, which is accompanied by the red shift of the absorption edge and excitonic luminescence band. The luminescence intensity increases when compared to the bare CdSe nanocrystals. After the CdSe/CdS nanocrystals have been stored under light for one day, a dramatic increase in luminescence is observed.

EXAMPLE 3

Preparation of CdTe:$Mn^{2+}$ Nanoparticles

Doped CdTe:$Mn^{2+}$ nanoparticles were prepared by a wet chemical technique which has been reported widely. Cadmium perchlorate hydrate (Aldrich), aluminum telluride (99.5% pure, Cerac), and thioglycolic (mercaptoacetic) acid (Aldrich) were used as received. CdTe nanoparticles were prepared by the rapid mixing of precursors containing cadmium perchlorate hydrate and sodium hydrotelluride (NaHTe), cooled to 5° C., under vigorous stirring. The $Cd^{2+}$ containing solution was prepared as follows: 0.70 g of $Cd(ClO_4)_2*H_2O$ and 0.05 g $Mn(ClO_4)_2*H_2O$ were dissolved in 125 mL of water. 0.3 mL of thioglycolic acid (TGA) was added to the solution and its pH was adjusted to ~11.2 by the addition of 0.1M NaOH. The solution was then purged with nitrogen for at least 30 minutes. The solution of NaHTe was prepared in a vessel cooled with water ice to 5° C., by bubbling an excess of $H_2Te$ through 22 mL of 0.05M NaOH for 40 minutes under nitrogen. The hydrogen telluride gas was obtained from the reaction of excessive amounts of $Al_2Te_3$ and 0.5M $H_2SO_4$ in an inert atmosphere (nitrogen). Great care was taken to keep the NaHTe solution temperature at an average of 5° C., as well as to avoid at all times any contact of the solutions with oxygen (air).

After the completion of the reaction, a yellow solution of CdTe nanocrystal nuclei was obtained. This solution was then refluxed at 100° C. to promote crystal growth. The size of the particles was controlled by the reaction time.

EXAMPLE 4

Preparation of $Y_2O_3:Eu^{3+}$ Nanoparticles

This method is according to Tao Ye, Zhao Guiwen, Zhang Weiping and Xia Shangda, "Combustion Synthesis and Photoluminescence of Nanocrystalline $Y_2O_3:Eu$ Phosphors", Materials Research Bulletin, 1997, 32, 501-506, the entire contents of which is herein explicitly incorporated by reference in its entirety. As an example, nitrates $Y(NO_3)_3.6H_2O$ and $Eu(NO_3)_3.6H_2O$ (Aldrich), and glycine $(NH_2CH_2COOH)$ (Alfa) were dissolved in distilled water and mixed in an appropriate molar ratio (Y:Eu:glycine=(1−x):x:1, where x is the molar doping ratio of $Eu^{3+}$, between 0 to 0.15), to form the precursor solution. The precursor solution was concentrated by heating in a porcelain crucible at 400° C. until excess free water evaporated and spontaneous ignition occurred. Within 10 seconds, the combustion was finished with the resultant ash of about 2 g (0.01 mol $Y_2O_3:Eu^{3+}$) filling the 200 ml container. These nanoparticle powders were then dissolved into water by ultrasound and different organic surface modifier agents such as thioglycolic (mercaptoacetic) acid (TGA) (Aldrich) are added for surface modification.

EXAMPLE 5

Preparation of a Silica Coating on $CdTe:Mn^{2+}$ Nanoparticles

Using $CdTe:Mn^{2+}/SiO_2$ as an example, the procedure for silica coating is as follows (M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497, the entire contents of which is herein explicitly incorporated by reference in its entirety): (1) To the $CdTe:Mn^{2+}$ nanoparticle solution (50 ml), a freshly prepared aqueous solution of 3-(mercaptopropyl) trimethoxysilane (MPS) (0.5 ml, 1 mM) (Sigma) is added under vigorous stirring. The function of MPS is that its mercapto group can directly bond to the surface Cd sites of CdTe, while leaving the silane groups pointing toward solution from where silicate ions approach the particle surface; (2) Addition of 2 ml of sodium silicate (Alfa) solution at pH of 10.5 under vigorous stirring; (3) The resulting dispersion (pH ~8.5) is allowed to stand for 5 days, so that silica slowly polymerized onto the particle surface; and (4) Transfer of the dispersion to ethanol so that the excess dissolved silicate can precipitate out, increasing the silica shell thickness.

EXAMPLE 6

Preparation of CdTe Nanoparticles Encapsulated with $BaFBr:Eu^{2+}$

The preparation of CdTe nanoparticles has been reported in N. Gaponik et. al., Thiol-Capping of CdTe Nanocrystals: An Alternative to Organometallic Synthetic Routes, J. Phys. Chem. B, 2002, 106: 7177-7185 and Joly et. al., Upconversion luminescence of CdTe nanoparticles, Phys. Rev. B, 2005, 71: 165304, the entire contents of both of which are herein explicitly incorporated by reference in its entirety. The particle sizes were controlled by using different thiol compounds. The average particle sizes stabilized by trifluoroacetic acid (TFA), L-cysteine, and thioglycolic acid (TGA) are around 3, 5, and 8 nm, respectively.

The procedures for making CdTe particles by these three thiol compounds are basically identical. Briefly, CdTe nanoparticles were prepared by the reaction of precursors containing cadmium perchlorate hydrate $[Cd(ClO_4)_2*H_2O]$ and hydrogen telluride $(H_2Te)$ under vigorous stirring. Here we give the recipe for making CdTe nanoparticles coated by TGA. The $Cd^{2+}$ containing solution was prepared as follows: 0.7311 g of $Cd(ClO_4)_2*H_2O$ was dissolved in 125 mL of water. TGA (0.396 mL) was added to the solution and the pH adjusted to ~11 by the addition of 0.1M NaOH. The solution was then purged with nitrogen for at least 30 minutes. $H_2Te$ gas was generated by the chemical reaction of excess aluminum telluride with 0.5 M sulfuric acid in an inert atmosphere (nitrogen) and was combined with the above solution containing $Cd^{2+}$ ions using the set-up as described in N. Gaponik et. al., Thiol-Capping of CdTe Nanocrystals: An Alternative to Organometallic Synthetic Routes, J. Phys. Chem. B, 2002, 106: 7177-7185, the entire contents of which is herein explicitly incorporated by reference in its entirety. After the completion of the reaction a yellow solution of CdTe nanocrystal nuclei was obtained. This solution was then refluxed at 100° C. to promote crystal growth. During the growth process, fractions with nanoparticles of different sizes may be extracted. The nanoparticles were extracted and stored at 4° C. in the dark. The particle concentration was approximately 2.82 mg/mL. The solid samples were obtained from the solutions by adding acetone with the precipitation carried out at 4° C. in order to avoid oxidation of the nanoparticles.

BaFBr and BaFBr:Eu phosphors were prepared by solid state diffusion. Calculated amounts of $BaF_2$, $BaBr_2$, and $EuCl_2$ were mixed thoroughly by stirring in an alcohol solution, the mixture was dried at room temperature and then placed in a crucible covered with carbon powder and heated at 880° C. for 2 hours. Next, a calculated amount of CdTe nanoparticle solution was mixed with BaFBr or $BaFBr:Eu^{2+}$ phosphors and heated at 100° C. in vacuum to make CdTe/BaFBr and $CdTe/BaFBr;Eu^{2+}$ nanocomposite phosphors. For example, 0.4 mL of TGA-stabilized nanoparticles (1.12 mg) was combined with 200 mg $BaFBr:Eu^{2+}$ with an $Eu^{2+}$ concentration of 2%. This gives a concentration of 0.6% CdTe by mass.

EXAMPLE 7

Optical Absorption and Photoluminescence of CdTe

Room temperature optical absorption spectra were taken with a Hewlett-Packard HP8453 spectrophotometer. The photoluminescence excitation and emission were recorded on a SPEX FLUOROLOG fluorescence spectrophotometer.

Figure 12:
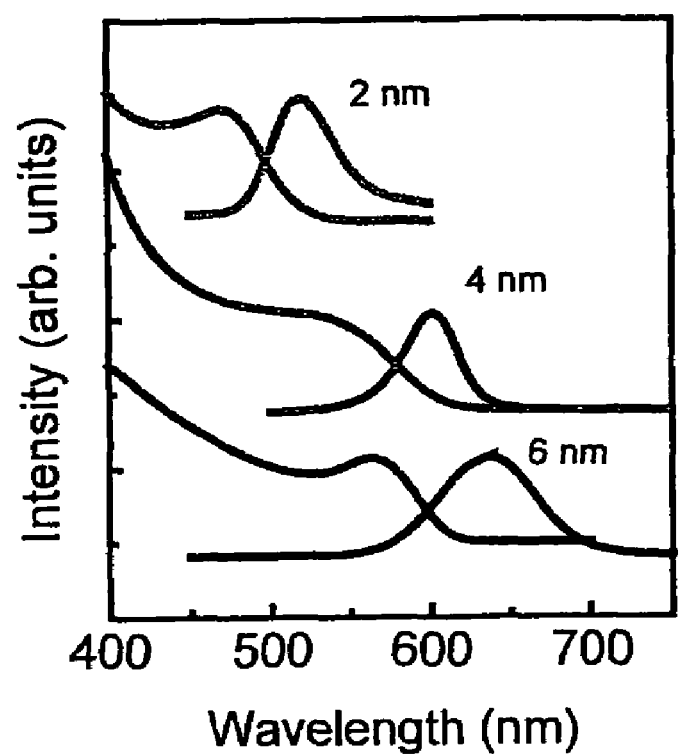
FIG. 12 shows the optical absorption (left) and emission (right) of the TFA-, L-cysteine- and TGA-coated CdTe nanoparticles with average sizes of 2, 4 and 6 nm, respectively.

FIG. 12 displays the optical absorption and emission spectra of the three CdTe nanoparticle samples in solution. All three solutions have pronounced absorptions peaking at 470 nm, 538 nm, and 570 nm, which are blue-shifted from the energy gap of bulk CdTe at 860 nm as a result of quantum size confinement. Using the effective mass approximation and the shift of the absorption edge, the particle sizes are estimated to be around 2, 4, and 6 nm for the three samples stabilized by TFA, L-cysteine, and TGA.

The CdTe nanoparticles show strong photoluminescence in both solution and as solids. The emission spectra of the solution samples are shown in FIG. 12 along with the absorption spectra. The emission maxima peak at 520, 602, and 638 nm, for the three samples stabilized by TFA, L-cysteine, and TGA. The emission maximum shifts to longer wavelengths with increasing size as a result of quantum size confinement.

EXAMPLE 8

Electron Microscopy of CdTe Nanoparticles

The identity, crystallinity, crystalline structure, size, and shape of the nanoparticles were determined by high-resolution transmission electron microscopy (HRTEM) and energy dispersive (EDS) analysis. The particles in solution were brought onto a lacey carbon film supported on a copper grid for HRTEM observations. The HRTEM images of the particles were obtained with a JEM 3000F transmission electron microscope (300 kV) with a structural resolution of 0.16 nm. The EDS spectra were recorded with an INCA system.

Figure 13:
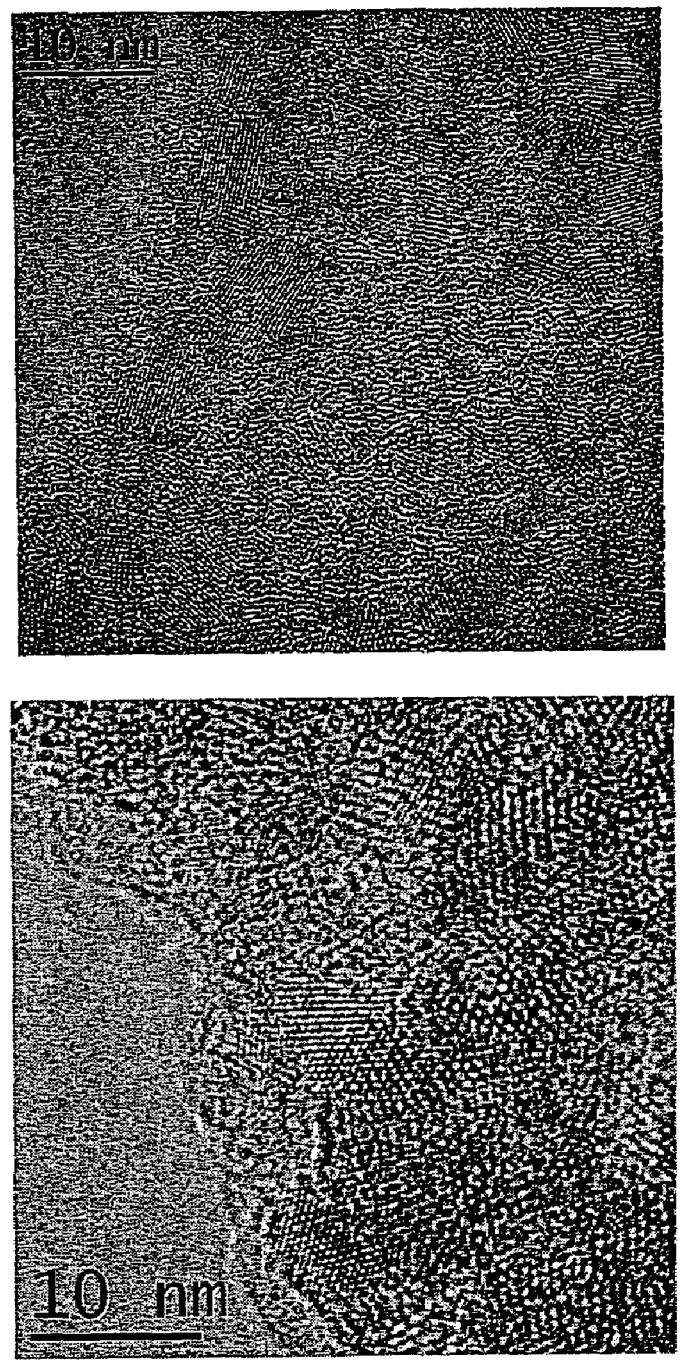
FIG. 13 shows high resolution transmission electron microscopy images of TFA- and L-cysteine-coated CdTe nanoparticles that show their average sizes of about 3 nm (top) and 5 nm (bottom), respectively.

To confirm the formation of CdTe nanoparticles, HRTEM images were used to observe the structure, size, and shape of the particles. The HRTEM images (FIG. 13) show that the average particle sizes of the TFA- and the L-cysteine coated nanoparticles are around 3 and 5 nm, in close agreement to the sizes estimated from optical absorption spectra. As observed in FIG. 13, most nanoparticles are spherical in shape. The [111] lattice spacing of the particles is estimated to be about 0.36 from the HRTEM images. This is in good agreement with the [111] spacing of cubic CdTe (0.374 nm).

EXAMPLE 9

Scintillation Luminescence of CdTe/BaFBr:$Eu^{2+}$ Nanocomposite Materials

The scintillation luminescence spectra were recorded using fiber optic cables connected to a fluorescence spectrometer (Ocean Optics). The samples were exposed to X-ray excitation using an X-ray chamber. The chamber is equipped with an Oxford Instruments XTF5011 X-ray tube with a tungsten target. Typically the X-ray tube was operated at 50 kVp and 1 mA.

Figure 14:
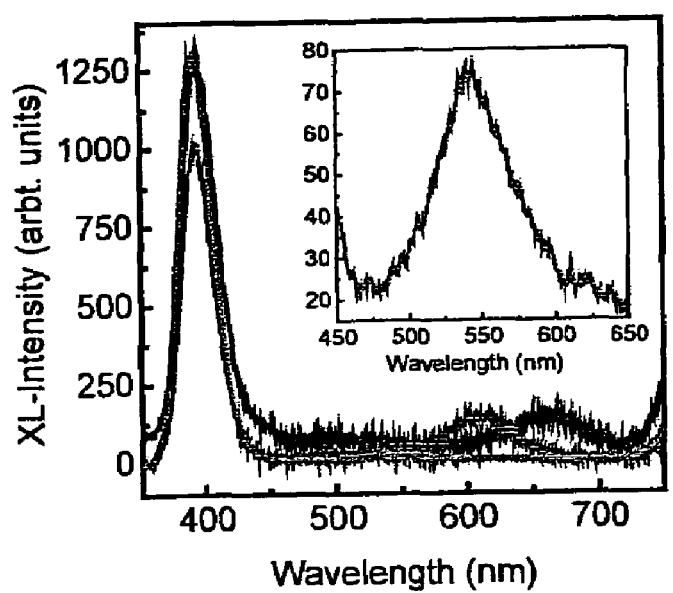
FIG. 14 shows the X-ray luminescence spectra of the TFA (green), L-cysteine (dark yellow) and TGA (red) coated CdTe nanoparticles in $BaFBr:Eu^{2+}$ phosphor, with emission near 550, 600, and 650 nm, respectively. The inset is the enlarged X-ray emission spectrum of the TFA-coated CdTe nanoparticles in $BaFBr:Eu^{2+}$ phosphor.

No X-ray excited luminescence was detected from the CdTe nanoparticles alone, either in solution or in solid form. However, in CdTe/BaFBr:$Eu^{2+}$ nanocomposite materials, intense X-ray luminescence is observed from both the CdTe nanoparticles and the $Eu^{2+}$ ions as displayed in FIG. 14. In FIG. 14, the emission at 390 nm is attributed to the $4f^65d^1$ ($2eg$)→$4f^7$ ($^8S_{7/2}$) transition of $Eu^{2+}$ in BaFBr:$Eu^{2+}$. The emissions at 541, 610, and 650 nm are from the CdTe nanoparticles stabilized by TFA, L-cysteine and TGA respectively. In these samples, the weight ratio of CdTe nanoparticles to BaFBr:$Eu^{2+}$ phosphor is about 0.3% (0.56 mg CdTe to 200 mg BaFBr:$Eu^{2+}$). Integrating the area under the peaks, the CdTe emission is approximately 20% of the $Eu^{2+}$ emission. Based on published data of 5.2 spontaneous photons emitted from BaFBr:$Eu^{2+}$ for every keV of X-ray absorbed (M. Thoms, H. von Seggern, Method for the determination of photostimulable defect center concentrations, production rates, and effective formation energies, J. Appl. Phys. 1994, 75: 4658-4661, the entire contents of which is herein explicitly incorporated by reference in its entirety.), this corresponds to about 50 photons emitted from CdTe for each 50 keV X-ray. Accordingly, we may conclude that the X-ray luminescence from the nanoparticles is quite efficient.

It is noted that the emission maxima of the emission peaks of the CdTe nanoparticles in CdTe/BaFBr:$Eu^{2+}$ nanocomposites shift to longer wavelengths compared to the emission peaks of the solution samples. For the TFA-coated particles, the shift is about 21 nm, for the L-cysteine coated sample, the shift is about 8 nm, and for the TGA-coated sample, the shift is about 12 nm. The emission red-shift of the solid samples from the solution samples is a common phenomenon and is attributed to particle-particle interactions. In addition, the nanoparticles may grow slightly larger during the heat treatment at 100° C. This is another possible reason for the red-shift of the nanoparticle emission in CdTe/BaFBr:$Eu^{2+}$ nanocomposites.

Since no X-ray luminescence is observed from CdTe nanoparticles either in solution or solid form, the X-ray luminescence from CdTe nanoparticles in CdTe/BaFBr:$Eu^{2+}$ materials is due to energy transfer from BaFBr:$Eu^{2+}$ to the CdTe nanoparticles. There are two possible mechanisms for the energy transfer from BaFBr:$Eu^{2+}$ phosphors to the CdTe nanoparticles. One is the transfer from $Eu^{2+}$ as the emission peak of $Eu^{2+}$ at 390 nm overlaps with the absorption band of the CdTe nanoparticles. Alternatively, the energy can transfer directly from the BaFBr host to the CdTe nanoparticles.

To reveal if the energy transfer from the BaFBr host to the CdTe nanoparticles is an efficient mechanism leading to X-ray luminescence from the particles, CdTe nanoparticles were encapsulated in BaFBr with no $Eu^{2+}$ present. In this case no X-ray luminescence was observed from the CdTe nanoparticles in the CdTe/BaFBr composites. This indicates that there is little energy transfer from the BaFBr host to the CdTe nanoparticles. The X-ray luminescence of CdTe in BaFBr:$Eu^{2+}$ phosphors is then likely due to the energy transfer from $Eu^{2+}$ ions.

EXAMPLE 10

Figure 15:
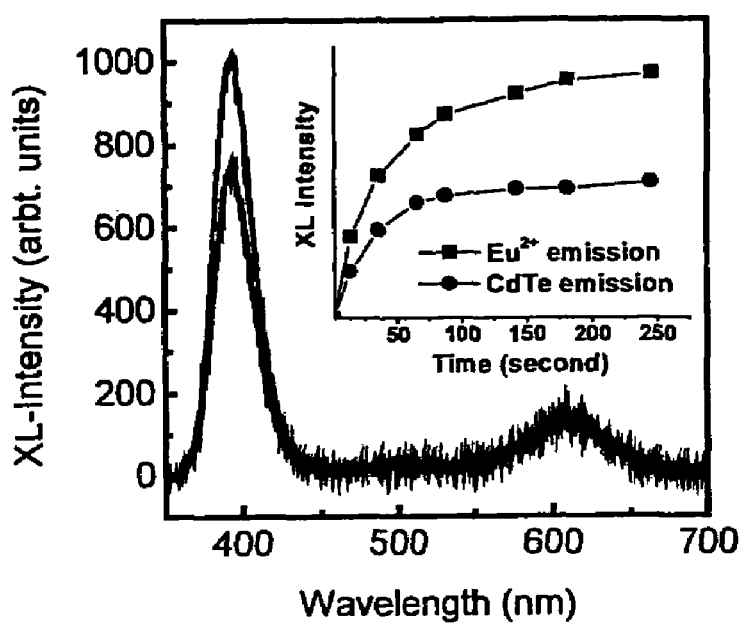
FIG. 15 shows the X-ray luminescence spectra of the L-cysteine coated CdTe particles (0.8 ml) in $BaFBr:Eu^{2+}$ phosphors (0.2 g) at zero (black) and 245 s (red) durations. The inset shows that the relative X-ray luminescence intensities of the $Eu^{2+}$ and CdTe emissions increase by 36% and 20%, respectively, as the X-ray exposure time increases.

Dose Dependence of Scintillation Luminescence of CdTe/BaFBr:Eu2+ Nanocomposite Materials FIG. 15 displays the X-ray spectra of CdTe/BaFBr:$Eu^{2+}$ nanocomposites prepared using a concentration of 0.8 ml L-cysteine stabilized CdTe particle solution in 0.2 g BaFBr:$Eu^{2+}$ phosphor. As the X-ray irradiation time increases, the X-ray luminescence intensity of $Eu^{2+}$ at 390 nm increases in intensity. This phenomenon has been discussed in W. Chen, S. P. Wang, S. Westcott, J. Zhang, A. G. Joly, and D. E. McCready, Structure and luminescence of BaFBr:$Eu^{2+}$ and BaFBr:$Eu^{2+}$, $Tb^{3+}$ phosphors and thin films, J. Appl. Phys. 2005, 97: 083506, the entire contents of which is herein explicitly incorporated by reference in its entirety.

In BaFX:$Eu^{2+}$ phosphors, the exciton emission of the host overlaps significantly with the absorption band of the $4f^7$ ($^8S_{7/2}$)→$4f^65d^1$ ($^2t^2g$) of $Eu^{2+}$ which enables the efficient energy transfer from the host to $Eu^{2+}$ ions and the emission from $Eu^{2+}$. Upon longer radiation exposure time or higher dose, more excitons are formed and this is likely the reason for the increase of the X-ray luminescence with increasing radiation time. If the X-ray luminescence of CdTe particles in CdTe/BaFBr:$Eu^{2+}$ composites is due to the energy transfer from $Eu^{2+}$, then the X-ray luminescence from the nanoparticles should change in intensity in the same manner as the $Eu^{2+}$ emission at 390 nm. As shown in FIG. 15, the nanoparticle emission does increase in intensity with increasing irradiation time and the increase rate is almost the same for the $Eu^{2+}$ emission at 390 nm and the particle emission at 610 nm. This indicates that there is likely energy transfer from $Eu^{2+}$ ions to CdTe nanoparticles in CdTe/BaFBr:$Eu^{2+}$ composites. However, for the samples with 0.2 and 0.4 ml CdTe particle solution in 0.2 g BaFBr:$Eu^{2+}$ phosphor, the $Eu^{2+}$ emission at 390 nm increased in intensity but the emission at 610 nm from the nanoparticles remains almost the same in intensity at different radiation durations.

EXAMPLE 11

Decay Lifetimes and Energy Transfer in CdTe/BaFBr:$Eu^{2+}$ Nanocomposite Materials The emission lifetimes and time-resolved spectra was collected using a nanosecond optical parametric oscillator/amplifer (Spectra-Physics MOPO-730) operating at a 10 Hz repetition rate and tunable between 220 nm and 1800 nm. The laser output was directed onto the particles and emission was collected at right angles to the excitation and focused into a ⅛-meter monochromator equipped with either a gated intensified CCD detector (for time-resolved spectra) or a standard photomultiplier tube (for lifetimes).

Figure 16:
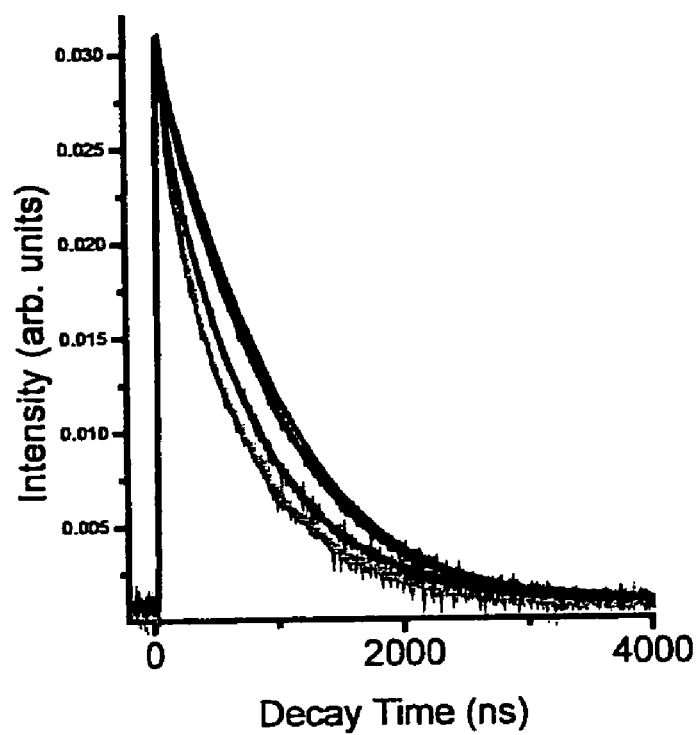
FIG. 16 shows the luminescence decay curves of $Eu^{2+}$ emission at 390 nm in $CdTe/BaFBr:Eu^{2+}$ nanocomposites. Red is 0.2 ml TFA-coated CdTe in 0.2 g $BaFBr:Eu^{2+}$; black, blue and green are 0.2, 0.4, and 0.8 ml L-cysteine-coated CdTe particles in 0.2 g $BaFBr:Eu^{2+}$, respectively. (also listed in order of decreasing decay time).

The $Eu^{2+}$ photoluminescence lifetimes of CdTe/BaFBr:$Eu^{2+}$ nanocomposites are shown in FIG. 16 following excitation at 281 nm. The decay lifetimes of $Eu^2+$ emission in CdTe/BaFBr:$Eu^{2+}$ nanocomposites are between 600 ns and 900 ns. For the two samples with 0.2 and 0.8 ml L-cysteine coated nanoparticles, the decay lifetimes of $Eu^{2+}$ at 390 nm are 710 and 610 ns, respectively. These lifetimes are shorter than the decay lifetime of $Eu^{2+}$ in BaFBr:$Eu^{2+}$ phosphors. The observed lifetime shortening is consistent with energy transfer from the $Eu^{2+}$ to the CdTe nanoparticles.

Figure 17:
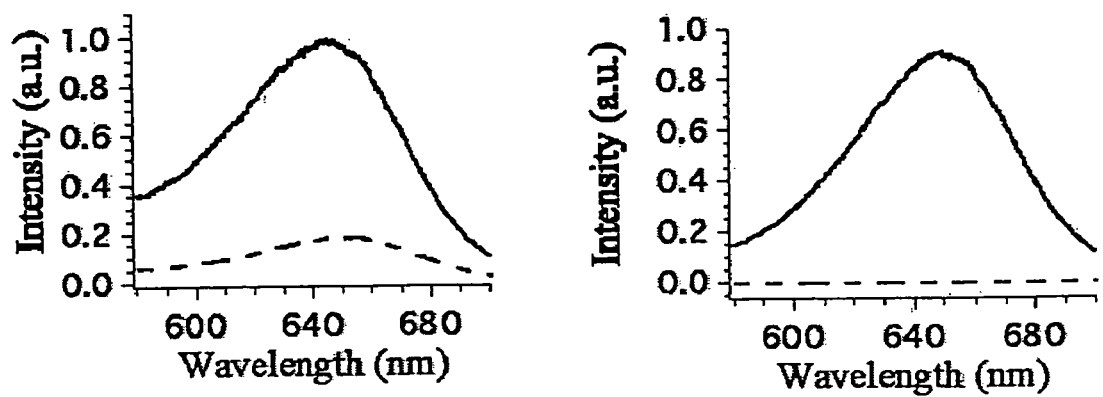
FIG. 17 shows the time-resolved luminescence spectra of CdTe particle emission from $CdTe/BaFBr:Eu^{2+}$ TGA coated particles at time delays of 0 ns (solid) and 500 ns (dotted) following excitation at 281 nm (left) and 415 nm (right). The gate width is 50 ns in all spectra.

FIG. 17 displays time-resolved emission spectra of CdTe/BaFBr:$Eu^{2+}$ TGA-coated nanocomposites at delay times of 0 and 500 ns and excitation wavelengths of 281 and 415 nm. Lower-energy excitation at 415 nm directly excites the CdTe nanoparticles and the emission lifetime is less than 50 ns. Therefore, the CdTe emission is not observed in the time-delayed (500 ns) spectrum. Excitation at 281 nm results in direct CdTe excitation as well as efficient excitation of the $Eu^{2+}$ through energy transfer from the host. In this case, because the CdTe emission lifetime is short compared with the $Eu^{2+}$ emission lifetime, the CdTe nanoparticles would display an emission lifetime identical with that of the $Eu^{2+}$ emission if energy transfer occurs. Therefore, excitation at 281 nm results in CdTe emission hundreds-of-nanoseconds after excitation as observed in FIG. 17.

Figure 18:
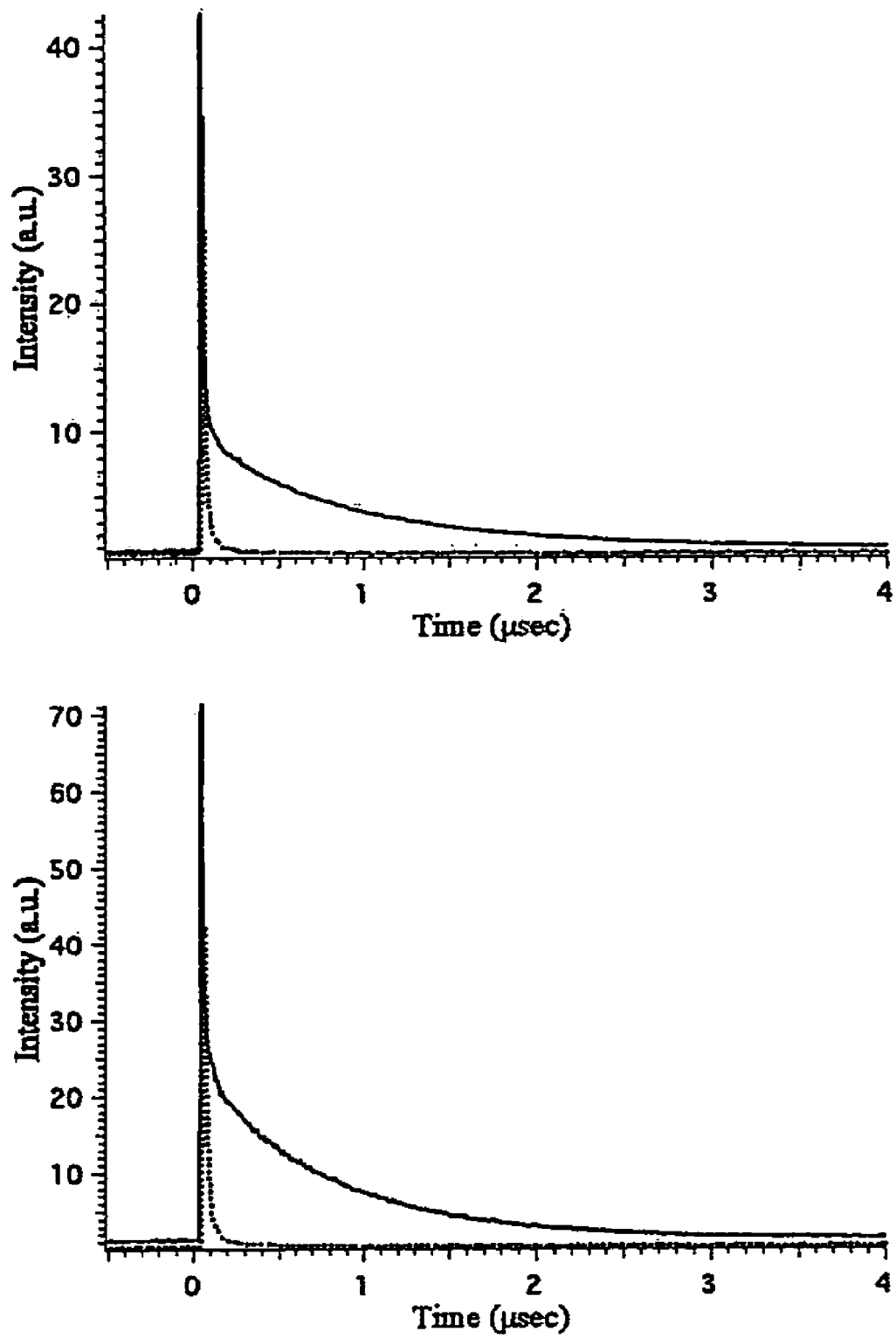
FIG. 18 shows the luminescence lifetimes from TGA-coated $CdTe/BaFBr:Eu^{2+}$ (0.4 mL CdTe in 0.2 g $BaFBr:Eu^{2+}$) particles (upper) and L-cysteine coated $CdTe/BaFBr:Eu^{2+}$ (0.4 mL CdTe in 0.2 g $BaFBr:Eu^{2+}$) particles (lower) following excitation at 281 nm (solid) and 415 nm (dotted).

The emission decay curves of the CdTe/BaFBr:$Eu^{2+}$ composites at 600 nm following 415 nm and 281 nm excitation are shown in FIG. 18. For excitation at 415 nm, FIG. 18 shows that the lifetimes of all the samples are similar and all are bi-exponential with a short component of about 2 nsec and a longer component of about 10 nsec. This is similar to the ultrafast decay behavior in pure CdTe nanoparticles. For excitation at 281 nm, FIG. 18 shows clearly that the emission of CdTe nanoparticles at 600 nm in the CdTe/BaFBr:$Eu^{2+}$ composites following 281 nm excitation exhibits both a long and short decay. The short decay (<15 ns) is due to the directly excited CdTe nanoparticles and is consistent with previous reports of lifetimes from CdTe nanoparticles. The long decay is almost identical to the decay lifetime of $Eu^{2+}$ emission at 390 nm, but clearly originates from the CdTe nanoparticles (FIG. 18) as it is at 600 nm. This indicates that there is indeed energy transfer from $Eu^{2+}$ ions to the particles and this energy transfer does affect the decay behavior of the nanoparticles.

EXAMPLE 12

Dosimetry Measurement

Figure 19:
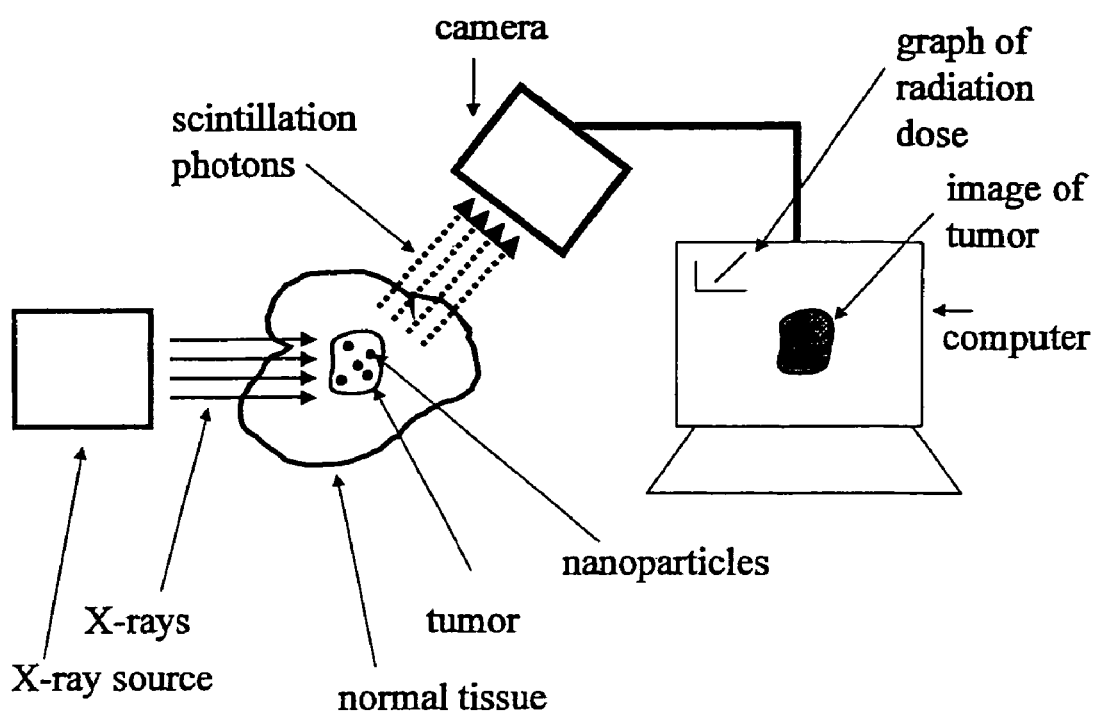
FIG. 19 shows a schematic depicting real-time measurement and imaging of radiation dose using scintillation luminescence.

Under this method, specially fabricated nanoparticles that emit SL upon exposure to X-rays are injected, either directly into tumors or into the bloodstream. In one embodiment, the nanoparticles have a coating or binding agent on their surface which is attracted to the tumor as described in EXAMPLE 13. Nanoparticles injected into the bloodstream travel to the tumors and become attached. By measuring the emission from these nanoparticles during radiation therapy as shown in FIG. 19, the X-ray dosage sustained by the tumor is assessed, thus allowing the nanoparticles to serve as a real-time dosimeter for radiation treatment. In one example, the expected relationship of decrease of SL intensity with radiation dose is used to calculate that the desired dose will have been received by the tumor when the SL intensity decreases to a certain percentage of the initial signal. Then during radiation therapy, the SL is monitored and when the desired decrease is observed, the radiation source can be turned off. Note that this is referenced to the initially measured SL signal rather than an expected initial SL signal. While being able to reference an expected signal would be useful, it may not be practical given different depths of tumors, tissue densities, nanoparticle attachment densities, and other factors. In another example, the expected change in relative peak heights for an SL with multiple emission peaks can be used similarly for monitoring the radiation dose received. In a third example, the change in emission wavelength may be used.

While a simple example of this technology would be to integrate the total scintillation emission from the area and determine the total dose, it is also possible to image the radiation dose by comparing the scintillation emission from different regions of the tissue. Using detection with spatial resolution allows for a two- or three-dimensional image of the radiation dosage received by the target. When the nanoparticles are targeted to the tumor, this also allows mapping of the extent and density of the tumor when radiation is applied to the entire area. If a different dose is required in different areas, this methodology allows for the mapping of the dose received in each area.

In vivo radiation detection requires stable nanoparticles in solution that are sensitive to radiation while producing strong scintillation luminescence with fast response and short afterglow. At the same time, these nanoparticles must have high solubility, little-to-no toxicity, biocompatibility, extended half-life in the bloodstream, and minimal non-specific targeting. Additionally, the emission wavelengths of these nanoparticles must be detectable through tissues, which will require nanoparticles that emit in a range from 700-1200 nm. The nanoparticles discussed here meet all of these requirements and are useful for the in vivo radiation measurement methods described herein. Radiation includes not only X-rays, but also gamma rays, protons, heavy particles such as neutrons, light ions such as carbon and neon, and pi-mesons.

Although the examples given here are with nanoparticles typically having dimensions less than 100 nm, it would be apparent to one of ordinary skill in the art that somewhat larger materials may also exhibit the desired properties for in situ radiation monitoring. For biological applications, one important property will be that the nanoparticles are small enough to pass through arteries or veins to the tumor or for direct injection to the tumor area. Such radiation monitoring may also be done using changes in SL in non-medical fields such as sterilization, radiation curing, doses received in space, manufacturing, security, inspection and non-destructive testing processes.

EXAMPLE 13

Nanoparticle Targeting to Tumor

Selective targeting systems can be divided into two main types, namely passive and active targeting, such as antigen-antibody targeting or receptor targeting. The passive targeting is based on the phenomenon known as the enhanced permeability and retention (EPR) effect. EPR is a common effect in solid tumors. The enhanced vascular permeability of a solid tumor is important in the biology of the tumor, which greatly impacts the targeted delivery of macromolecular anticancer drugs.

In this example, we particularly discuss active targeting, which consists of selective delivery of agents by conjugates containing a receptor-targeting moiety (J. Sudimack and R. J. Lee, Targeted drug delivery via the folate receptor, Advanced Drug Delivery Reviews, 2000, 41: 147-162 and C. P. Leamon and J. A. Reddy, Folate-targeted chemotherapy, Advanced Drug Delivery Reviews, 2004, 56: 1127-1141, the entire contents of both of which are herein explicitly incorporated by reference in its entirety). The method is similar to antibody-antigen targeting (bioconjugation with a biomolecule) and is in some ways better suited for nanoparticles than passive targeting. Here an ovarian tumor is used as an example for nanoparticle targeting. Similar methods can be used for other types of tumor targeting as well.

Folic acid targeting is a highly specific binding event, just like a key (folic acid) inserting into a lock (folate receptor) (J. Sudimack and R. J. Lee, Targeted drug delivery via the folate receptor, Advanced Drug Delivery Reviews, 2000, 41: 147-162, the entire contents of which is herein explicitly incorporated by reference in its entirety). In order to deliver SL nanoparticles to ovarian tumors with folic acid, folic acid (a ligand) must be stably linked to the nanoparticles, typically by a chemical (covalent) bond. Because folic acid retains its receptor binding properties when derivatized via its $\gamma$-carboxyl (C. P. Leamon and J. A. Reddy, Folate-targeted chemotherapy, Advanced Drug Delivery Reviews, 2004, 56: 1127-1141, the entire contents of which is herein explicitly incorporated by reference in its entirety), nanoparticles should be linked to the $\gamma$-carboxyl group of folic acid.

Although the foregoing invention has been described in some detail by way of illustration and example for purposes of clarity of understanding, it will be obvious to those skilled in the art that certain changes and modifications may be practiced without departing from the spirit and scope thereof; as described in this specification and as defined in the appended claims below.

REFERENCES

The following references, to the extent that they provide exemplary procedural or other details supplementary to those set forth herein, are specifically incorporated herein by reference in their entirety as though set forth herein in particular.

1. W. Chen, X. Zhang, Y. Huang, Luminescence Enhancement of EuS Clusters in USY-Zeolite, Appl. Phys. Lett. 2000, 76 (17): 2328-2330.
2. M. A. Correa-Duarte, M. Giesig, and L. M. Liz-Marzan, Stabilization of CdS semiconductor nanoparticles against photodegradation by a silica coating procedure, Chem. Phys. Lett., 1998, 286: 497.
3. Y. Zhang, N. Kohler, M. Zhang, Surface modification of superparamagnetic magnetite nanoparticles and their intracellular uptake, Biomaterials 23, 1553-1561 (2002).
4. Shaopeng Wang, Natalia Mamedova, Wei Chen, Joel Studer, and Nicholas A. Kotov, Antigen/Antibody Immunocomplex from CdTe Nanoparticle Bioconjugates, Nanoletters, 2002, 2(8): 817-822.
5. X. G. Peng, M. C. Schlamp, A. V. Kadavanich and A. P. Alivisatos, "Epitaxial Growth of Highly Luminescent CdSe/CdS Core/Shell Nanocrystals with Photostability and Electronic Accessibility" J. Am. Chem. Soc., 119, 7019 (1997).
6. Tao Ye, Zhao Guiwen, Zhang Weiping and Xia Shangda, "Combustion Synthesis and Photoluminescence of Nanocrystalline Y2O3:Eu Phosphors", Materials Research Bulletin, Vol. 32, No. 5, pp. 501-506, 1997.
7. N. Gaponik, D. Talapin, A. L. Rogach, K. Hoppe, E. V. Shevchenko, A. Kornowski, A. Eychmuller and H. Weller, Thiol-Capping of CdTe Nanocrystals: An Alternative to Organometallic Synthetic Routes, J. Phys. Chem. B, 2002, 106: 7177-7185.
8. G. Joly, W. Chen, D. E. McCready, J-O Malm, and J-O. Bovin, Upconversion luminescence of CdTe nanoparticles, Phys. Rev. B 2005, 71:165304.
9. M. Thoms, H. von Seggern, Method for the determination of photostimulable defect center concentrations, production rates, and effective formation energies, J. Appl. Phys. 1994, 75: 4658-4661.
10. W. Chen, S. P. Wang, S. Westcott, J. Zhang, A. G. Joly, and D. E. McCready, Structure and luminescence of BaFBr:Eu2+ and BaFBr:Eu2+, Tb3+ phosphors and thin films, J. Appl. Phys. 2005, 97: 083506.
11. J. Sudimack and R. J. Lee, Targeted drug delivery via the folate receptor, Advanced Drug Delivery Reviews, 2000, 41: 147-162.
12. C. P. Leamon and J. A. Reddy, Folate-targeted chemotherapy, Advanced Drug Delivery Reviews, 2004, 56: 1127-1141.
13. W. Chan, D. J. Maxwell, X. Gao, R. E. Bailey, M. Y. Han, and S. M. Nie, Luminescent quantum dots for multiplexed biological detection and imaging, Current Opinion in Biotechnology, 13, 40-46 (2002).
14. M. Gurvich, C. Hall, I. A. Kamenskikh, I. H. Muro, V. V. Mikhilin and J. S. Worgan, Phosphors for luminescent imaging plates, Journal of X-ray science and technology, 1996, 6: 48-62.
15. W. E. van Eijk, Inorganic scintillators in medical imaging, Physics in Medicine and Biology, 2002, 47: R85-R106.
16. U.S. Pat. Nos. 6,300,640, 5,952,665, 5,656,815 and 5,606,163. U.S. published patent application No. 20030064532.

What we claim is:
1. A method for determining the amount of ionizing radiation dosage received by a target, comprising the steps of:
   placing a scintillator nanomaterial adjacent to a target, wherein the scintillator nanomaterial has a luminescent response to ionizing radiation that varies with the ionizing radiation dosage received;

detecting the luminescence generated by the scintillator nanomaterial, wherein the luminescence is generated in the absence of one or more secondary excitation sources, the one or more secondary excitation sources being selected from the group consisting of thermal and optical excitation sources;

analyzing the detected luminescence in order to determine the ionizing radiation dosage received by the target.

2. The method of claim 1, wherein the luminescent response varies in intensity depending on the total ionizing radiation dosage received by the target.

3. The method of claim 2, wherein the luminescent response variation is linear.

4. The method of claim 1, wherein the luminescent response varies in peak wavelength depending on the total ionizing radiation dosage received by the target.

5. The method of claim 1, wherein the luminescent response varies in relative intensities of two or more luminescent peaks depending on the total ionizing radiation dosage received by the target.

6. The method of claim 1, wherein the nanomaterial is a semiconductor nanoparticle.

7. The method of claim 6, wherein the semiconductor nanoparticle is chosen from the group consisting of PbS, PbSe, PbTe, Si, CdS, CdSe, CdTe, ZnS, ZnSe, ZnO, InP, InAs, CdTe/CdSe core/shell, and CdSe/CdS core shell nanoparticles.

8. The method of claim 1, wherein the nanomaterial is a doped nanoparticle comprising a host nanoparticle and at least one dopant.

9. The method of claim 8, wherein the host nanoparticle is selected from the group consisting of ZnS, ZnSe, ZnO, MgS, $TiO_2$, $Y_2O_3$, CdTe, CdSe, CdS, GaS, SrS, BaS, $CaF_2$, BaFBr, $Zn_2SiO_4$ and $Zn_xMg_{1-x}S$, where $0 \leq x \leq 1$.

10. The method of claim 8, wherein the dopants are selected from the group consisting of $Nd^{3+}$, $Yb^{3+}$, $Pr^{3+}$, $Mn^{2+}$, $Eu^{2+}$, $Cr^{3+}$, $Tb^{3+}$, and $Ce^{3+}$.

11. The method of claim 1, wherein the nanomaterial is an energy-transfer nanocomposite comprising a nanoparticle, wherein the nanoparticle is encapsulated in a material having a high absorption coefficient for radiation and an ability to transfer energy to the nanoparticle.

12. The method of claim 11, wherein the encapsulating material has the general formula $AB_xC_{2-x}$ where A is Ba, Sr, or Ca; B is F, Cl, Br, or I; C is F, Cl, Br, or I, and $0 \leq x \leq 2$.

13. The method of claim 11, wherein the encapsulating material further comprises at least one dopant element.

14. The method of claim 13, wherein the at least one dopant element is selected from the group consisting of rare earth ions, transition metal ions, oxygen, and halides.

15. The method of claim 11, wherein the nanoparticle is represented by the formula $(M_{1-z}N_z)_{1-x}A_{1-y}B_y$, where M=Zn, Cd, Hg, Pb, Ca, Ba, Sr, and Mg; N=Zn, Cd, Hg, Pb, Ca, Ba, Sr, and Mg; A=S, Se, Te, and O; B=S, Se, Te, and O, wherein $0 \leq x < 1$, $0 < y \leq 1$, $0 < z \leq 1$.

16. The method of claim 11, wherein the nanoparticle is selected from the group consisting of $Y_2O_3$ and $Zn_2SiO_4$.

17. The method of claim 11, wherein the nanoparticle further comprises at least one dopant element.

18. The method of claim 17, wherein the at least one dopant element is selected from the group consisting of rare earth ions, transition metal ions, and halides.

19. The method of claim 1, wherein the step of detecting the luminescence generated by the scintillator nanomaterial, wherein the luminescence is generated in the absence of one or more secondary excitation sources, the one or more secondary excitation sources being selected from the group consisting of thermal and optical excitation sources, is performed utilizing spatial resolution, thereby allowing for a two- or three-dimensional image of the ionizing radiation dosage received by the target.

20. The method of claim 1, wherein the scintillator nanomaterial is implanted, thereby allowing for an in vivo measurement.

21. The method of claim 1, further comprising the step of injecting the scintillator nanomaterial into a bloodstream of a subject.

22. The method of claim 1, further comprising the steps of:
treating the scintillator nanomaterial such that it is capable of binding to a target
injecting the scintillator nanomaterial into the bloodstream of a subject; and
allowing the scintillator nanomaterial to travel through the bloodstream such that the scintillator nanomaterial reaches and binds to the target.

23. The method of claim 22, wherein the scintillator nanomaterial is treated in a manner selected from the group of treatments consisting of bioconjugation with a biomolecule, antibody, or antigen, and chemical binding to a ligand that can bind to a receptor on the target.

24. The method of claim 1, wherein at least one component of the luminescent response occurs at wavelengths between 700-1200 nm.

25. The method of claim 1, wherein the ionizing radiation dosage received by the target is determined within a time of from about 1 second to 1 minute.

26. A method for determining the amount of ionizing radiation dosage received by a target, comprising the steps of:
placing a scintillator nanomaterial adjacent to a target, wherein the scintillator nanomaterial has a luminescent response to ionizing radiation that varies in intensity with dose rate but does not vary with total dosage;
detecting the luminescent response of the scintillator nanomaterial, wherein the luminescence is generated in the absence of one or more secondary excitation sources, the one or more secondary excitation sources being selected from the group consisting of thermal and optical excitation sources;
integrating the detected luminescent response of the scintillator nanomaterial in order to determine the ionizing radiation dosage received by the subject.

* * * * *